(12) United States Patent
Setti

(10) Patent No.: US 7,368,476 B2
(45) Date of Patent: *May 6, 2008

(54) HYDROXAMATES AS THERAPEUTIC AGENTS

(75) Inventor: Eduardo L. Setti, San Mateo, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 11/100,781

(22) Filed: Apr. 7, 2005

(65) Prior Publication Data

US 2005/0227976 A1    Oct. 13, 2005

Related U.S. Application Data

(60) Provisional application No. 60/560,108, filed on Apr. 7, 2004.

(51) Int. Cl.
*A61K 31/34* (2006.01)
*C07D 307/00* (2006.01)

(52) U.S. Cl. ............... 514/469; 514/320; 514/337; 549/469; 546/196; 546/205; 546/284.1

(58) Field of Classification Search ........... 514/232.8, 514/469, 337, 320; 546/196, 284.1, 205; 549/469; 544/153
See application file for complete search history.

(56) References Cited

U.S. PATENT DOCUMENTS

2005/0187261 A1 *  8/2005  Verner et al. ............... 514/350

FOREIGN PATENT DOCUMENTS

WO    WO 2004092115 A2 * 10/2004

* cited by examiner

*Primary Examiner*—Rei-tsang Shiao
(74) *Attorney, Agent, or Firm*—Wilson, Sonsini, Goodrich & Rosati

(57) ABSTRACT

The present invention is directed to certain hydroxamate derivatives that are inhibitors of histone deacetylase and are therefore useful in the treatment of diseases associated with histone deacetylase activity. Pharmaceutical compositions and processes for preparing these compounds are also disclosed.

13 Claims, No Drawings

HYDROXAMATES AS THERAPEUTIC AGENTS

CROSS REFERENCE

This application claims priority under 35 USC § 119(e) to U.S. provisional application Ser. No. 60/560,108, filed Apr. 7, 2004, the disclosure of which is incorporated herein by reference in its entirety.

BACKGROUND OF THE INVENTION

1. Field of the Invention

The present invention is directed to certain hydroxamate derivatives that are inhibitors of histone deacetylase and are therefore useful in the treatment of diseases associated with histone deacetylase activity. Pharmaceutical compositions and processes for preparing these compounds are also disclosed.

2. State of the Art

Interest in histone deacetylase enzymes (HDACs) as targets for pharmaceutical development has centered on the role of HDACs in regulating genes associated with cell-cycle progression and the development and progression of cancer (reviewed in Kramer et. al. 2001. *Trends Endocrinol. Metab.* 12:294-300). Several studies have shown that treatment of various cell lines with HDAC inhibitors leads to hyper acetylation of histone proteins and cell-cycle arrest in late $G_1$ phase or at the $G_2$/M transition. Genes involved in the cell cycle that have been shown to be up regulated by HDAC inhibitors include p21, p27, p53 and cyclin E. Cyclin A and cyclin D have been reported to be down regulated by HDAC inhibitors. In tumor cell lines, several studies have shown that treatment with HDAC inhibitors can lead to growth inhibition, growth arrest, terminal differentiation and/or apoptosis. In vivo studies have demonstrated growth inhibition of tumors and a reduction in tumor metastasis as a result of treatment with HDAC inhibitors.

The clearest link between abnormal HDAC activity and cancer occurs in acute promyelocytic leukemia. In this condition, a chromosomal translocation leads to the fusion of the retinoic acid receptor RARα with the promyelocytic leukemia (PML) or promyelocytic leukemia zinc-finger (PLZF) proteins. Both PML-RARα and PLZF-RARα promote the progression of leukemia by repressing retinoic acid-regulated genes through the abnormal recruitment of SMRT-mSin3-HDAC complex (Lin et. al., 1998, *Nature* 391:811-814; Grignani et al., 1998, *Nature* 391:815-818). Whereas the PML-RARα form of the disease is treatable with retinoic acid, the PLZF-RARα form is resistant to this treatment. For a patient with the retinoic acid-resistant form of the disease, the addition of the HDAC inhibitor sodium butyrate to the dosing regimen led to complete clinical and cytogenic remission (Warrell et al., 1998, *J. Natl.Cancer-.Inst.* 90:1621-1625). HDACs have also been associated with Huntington's disease (Steffan, et al., *Nature* 413:739-744, "Histone deacetylase inhibitors arrest polyglutamine-dependent neurodegeneration in *Drosophila*").

In summary, an increase in HDAC activity contributes to the pathology and/or symptomatology of a number of diseases. Accordingly, molecules that inhibit the activity of HDAC are useful as therapeutic agents in the treatment of such diseases.

SUMMARY OF THE INVENTION

In a first aspect, this invention provides a compound of Formula (I):

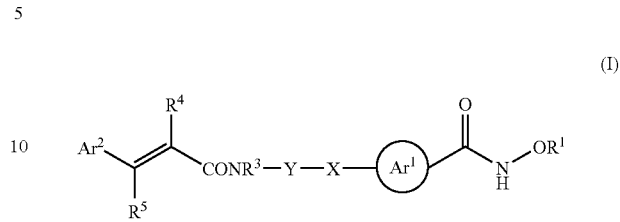

wherein:
$R^1$ is hydrogen or alkyl;
X is —O—, —$NR^2$—, or —$S(O)_m$ where m is 0-2 and $R^2$ is hydrogen or alkyl;
Y is alkylene;
$Ar^1$ is phenylene or heteroarylene wherein said $Ar^1$ is optionally substituted with one or two groups independently selected from alkyl, halo, hydroxy, alkoxy, haloalkoxy, or haloalkyl;
$R^3$ is hydrogen, alkyl, hydroxyalkyl, or alkoxyalkyl;
$Ar^2$ is aryl or heteroaryl; and
one of $R^4$ and $R^5$ is hydrogen or alkyl and the other is —$CHR^6$ where $R^6$ is aryl, heteroaryl, heterocycloalkyl, hydroxyalkyloxy, alkoxyalkyloxy, aminoalkyloxy, aryloxy, aralkyloxy, heteroaryloxy, heteroaralkyloxy, heterocycloalkyloxy, heterocycloalkylalkyloxy, alkoxyalkyl-$S(O)_n$—, hydroxyalkyl-$S(O)_n$—, —$S(O)_n$-aryl, aralkyl-$S(O)_n$—, —$S(O)_n$-heteroaryl, heteroaralkyl-$S(O)_n$—, —$S(O)_n$-heterocycloalkyl, heterocycloalkylalkyl-$S(O)_n$— (where n is 0, 1, or 2), —$NR^7R^8$ (where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl), —$NR^9SO_2R^{10}$ (where $R^9$ is hydrogen or alkyl and $R^{10}$ is alkyl, aryl, aralkyl, heteroaryl, heteroaralkyl, heterocycloalkyl, or heterocycloalkylalkyl), or —$NR^{11}COR^{12}$ (where $R^{11}$ is hydrogen or alkyl and $R^{12}$ is alkyl, aryl, aralkyl, heteroaryl, heteroaralkyl, heterocycloalkyl, or heterocycloalkylalkyl); or
a pharmaceutically acceptable salt thereof.

In a second aspect, this invention is directed to a pharmaceutical composition comprising a therapeutically effective amount of a compound of Formula (I) or pharmaceutically acceptable salts thereof and a pharmaceutically acceptable excipient.

In a third aspect, this invention is directed to a method for treating a disease in an animal mediated by HDAC which method comprises administering to the animal a pharmaceutical composition comprising a therapeutically effective amount of a compound of Formula (I) or a pharmaceutically acceptable salt thereof and a pharmaceutically acceptable excipient. Preferably, the disease is a proliferative disorder such as cancer and bipolar disorders and the animal is human. Preferably, the cancer is prostate cancer, breast cancer, lung melanoma, stomach cancer, neuroblastoma, colon cancer, pancreatic cancer, ovarian cancer, T-cell lymphoma, or leukemia such as myelogenous leukemia (MM) and acute myelogenous leukemia (AML).

In a fourth aspect, this invention is directed to a method for treating cancer in an animal which method comprises administering to the animal a pharmaceutical composition comprising a therapeutically effective amount of a compound of Formula (I) or a pharmaceutically acceptable salt thereof and a pharmaceutically acceptable excipient in combination with radiation therapy and optionally in combination with one or more compound(s) independently selected from an estrogen receptor modulator, an androgen receptor modulator, retinoid receptor modulator, a cytotoxic agent, another antiproliferative agent, a prenyl-protein transferase inhibitor, an HMG-CoA reductase inhibitor, an HIV protease inhibitor, a reverse transcriptase inhibitor, an angiogenesis inhibitor, or DNA methyl transferase inhibitor.

In a fifth aspect, this invention is directed to an intermediate of Formula (II):

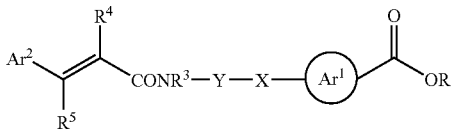

where $Ar^1$, $Ar^2$, $R^3$, $R^4$, $R^5$, X and Y are as defined for (I) above and R is hydrogen or alkyl. Preferably, $Ar^1$, $Ar^2$, $R^3$, $R^4$, $R^5$, X and Y are as defined in Preferred embodiments below.

In a sixth aspect, this invention is directed to a process of preparing a compound of Formula (I) comprising:

(i) reacting a compound of Formula (III):

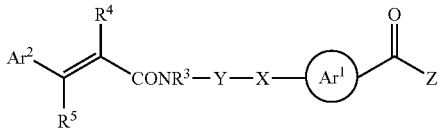

where Z is hydroxyl, halo, alkoxy or succinimido ester with a hydroxylamine of formula $NH_2OR$ where $R^1$ is hydrogen, alkyl, or an oxygen protecting group;

(ii) optionally removing $R^1$ group to give a compound of Formula (I) where $R^1$ is hydrogen;

(iii) optionally forming an acid addition or base salt;

optionally forming free base from an acid addition salt; or (iv) optionally modifying any of the X, $R^1$, $R^2$, $R^3$, $R^4$, $Ar^1$ and $Ar^2$ groups.

In a seventh aspect, this invention is directed to the use of a compound of Formula (I) or a pharmaceutically acceptable salt thereof in the manufacture of a medicament. Preferably, the medicament is for use in the treatment of cancer.

DETAILED DESCRIPTION OF THE INVENTION

Definitions:

Unless otherwise stated, the following terms used in the specification and claims are defined for the purposes of this Application and have the following meanings:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, propylthio (including all isomeric forms), butylthio (including all isomeric forms), and the like.

"Alkylsulfonyl" means a —$SO_2R$ radical where R is alkyl as defined above, e.g., methylsulfonyl, ethylsulfonyl, and the like.

"Amino" means a —$NH_2$

"Alkylamino" means a —NHR radical where R is alkyl as defined above, e.g., methylamino, ethylamino, n-, iso-propylamino, n-, iso-, tert-butylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxycarbonyl" means a —C(O)OR radical where R is alkyl as defined above, e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" means a —OR radical where R is alkoxyalkyl as defined above, e.g., methoxyethoxy, 2-ethoxyethoxy, and the like.

"Alkoxyalkyloxyalkyl" means a-(alkylene)-R radical where R is alkoxyalkyloxy as defined above, e.g., methoxyethoxymethyl, 2-ethoxyethoxymethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —$COR^a$ where $R^a$ is alkyl, and R' are independently selected from hydrogen, alkyl, hydroxyalkyl, alkoxyalkyl, optionally substituted phenyl, optionally substituted phenylalkyl, optionally substituted heteroaryl, optionally substituted heteroaralkyl, or haloalkyl, e.g., aminomethyl, methylaminoethyl, 2-ethylamino-2-methylethyl, 1,3-diaminopropyl, dimethylaminomethyl, diethylaminoethyl, acetylaminopropyl, and the like.

"Aminoalkoxy" means a —OR radical where R is aminoalkyl as defined above, e.g., 2-aminoethoxy, 2-dimethylaminopropoxy, and the like.

"Aminocarbonyl" means a —CONRR radical where each R is independently hydrogen or alkyl as defined above, e.g., —$CONH_2$, methylaminocarbonyl, 2-dimethylaminocarbonyl, and the like.

"Acylamino" means a —NHCOR radical where R is alkyl as defined above, e.g., acetylamino, propionylamino, and the like.

"Aryl" means a monovalent monocyclic or bicyclic aromatic hydrocarbon radical of 6 to 12 ring atoms e.g., phenyl, naphthyl or anthracenyl. Unless stated otherwise, the aryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted phenylalkyl, optionally substituted heteroaryl, cycloalkyloxy, cycloalkenyloxy, optionally substituted phenylcarbonylamino, optionally substituted heteroaryloxy, optionally substituted heteroaralkyloxy, aminoalkyl, aminoalkoxy, alkoxyalkyl, alkoxyalkyloxy, methylenedioxy, alkylsulfonyl, haloalkoxyalkyl, optionally substituted phenyloxyalkyl, optionally substituted heteroaryloxyalkyl, optionally substituted heterocycloalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)n-R$^a$ (where n is 0 to 2 and R$^a$ is alkyl, haloalkyl, hydroxyalkyl, alkoxyalkyl, optionally substituted phenyl, optionally substituted phenylalkyl, optionally substituted heteroaryl, or optionally substituted heteroaralkyl), -alkylene-NHSO$_2$-R$^b$ (where R$^b$ is alkyl, haloalkyl, optionally substituted phenyl, optionally substituted phenylalkyl, optionally substituted heteroaryl, optionally substituted heteroaralkyl, or optionally substituted heterocycloalkyl), -alkylene-NHCO-R$^c$ (where R$^c$ is alkyl, haloalkyl, optionally substituted phenyl, optionally substituted phenylalkyl, optionally substituted heteroaryl, optionally substituted heteroaralkyl, or optionally substituted heterocycloalkyl), or -(alkylene)$_{n1}$—CONR$^f$R$^g$ (where n1 is 0 or 1, R$^f$ is hydrogen, alkyl, or hydroxyalkyl and R$^g$ is hydrogen, alkyl, hydroxyalkyl, alkoxyalkyl, optionally substituted phenyl, optionally substituted phenylalkyl, optionally substituted heteroaryl, optionally substituted heteroaralkyl, or optionally substituted heterocycloalkylalkyl, or R$^f$ and R$^g$ together with the nitrogen atom to which they are attached from heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. Preferably, the substitutents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)-ethoxy, methoxymethyl, phenoxymethyl, 2-morpholino-4-ylethyl, morpholino-4-ylmethyl, N,N-dimethylaminomethyl, i-propoxymethyl, or phenoxymethyl.

"Aryloxy" means a —OR radical where R is aryl as defined above, e.g., phenyloxy, and the like.

"Aralkyl" means a -(alkylene)-R radical where R is aryl as defined above.

"Aralkyloxy" means a —OR radical where R is aralkyl as defined above, e.g, benzyloxy, and the like.

"Cycloalkyl" means a cyclic saturated monovalent hydrocarbon radical of three to ten carbon atoms, e.g., cyclopropyl, cyclobutyl, cyclopentyl, cyclohexyl, or adamantyl. The cycloalkyl is optionally substituted with optionally substituted phenyl.

"Cycloalkenyl" means an cyclic unsaturated monovalent hydrocarbon radical of three to six carbon atoms, e.g., cyclopropenyl, cyclobutenyl, cyclohexenyl, and the like.

"Cycloalkyloxy" means a —OR radical where R is cycloalkyl as defined above, e.g., cyclopropyloxy, cyclohexyloxy, and the like.

"Cycloalkenyloxy" means a —OR radical where R is cycloalkenyl as defined above, e.g., cyclopropenyloxy, cyclohexenyloxy, and the like.

"Carboxyalkylaminoalkyl" means a -(alkylene)-NH-(alkylene)-COOH radical, e.g., carboxyethylaminomethyl, and the like.

"Dialkylamino" means a —NRR' radical where R and R' are independently alkyl as defined above, e.g., dimethylamino, diethylamino, methylpropylamino, methylethylamino, n-, iso-, or tert-butylamino, and the like.

"Halo" means fluoro, chloro, bromo, and iodo, preferably fluoro or chloro.

"Haloalkyl" means alkyl substituted with one or more halogen atoms, preferably one to five halogen atoms, preferably fluorine or chlorine, including those substituted with different halogens, e.g., —CH$_2$Cl, —CF$_3$, —CHF$_2$, —CF$_2$CF$_3$, —CF(CH$_3$)$_3$, and the like.

"Haloalkoxy" means a —OR radical where R is haloalkyl as defined above e.g., —OCF$_3$, —OCHF$_2$, and the like.

"Haloalkoxyalkyl" means a -(alkylene)-OR radical where R is haloalkyl as defined above e.g., trifluoromethyloxymethyl, 2,2,2-trifluoroethyloxymethyl, 2-trifluoromethoxyethyl, and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" or "hydroxyalkyloxy" means a —OR radical where R is hydroxyalkyl as defined above.

"Hydroxyalkoxyalkyl" means a -(alkylene)-OR radical where R is hydroxyalkyl as defined above e.g., hydroxymethyloxymethyl, hydroxyethyloxymethyl, and the like.

"Heterocycloalkyl" means a saturated or unsaturated monovalent cyclic group of 3 to 8 ring atoms in which one or two ring atoms are heteroatoms selected from N, O, or S(O)$_n$, where n is an integer from 0 to 2, the remaining ring atoms being C. One or two ring carbon atoms can optionally be replaced by a —CO— group. More specifically the term heterocycloalkyl includes, but is not limited to, pyrrolidino, piperidino, morpholino, piperazino, tetrahydropyranyl, and thiomorpholino, and the derivatives thereof and N-oxide or a protected derivative thereof. The heterocycloalkyl is optionally fused to aryl. Unless stated otherwise, the heterocyloalkyl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, optionally substituted phenylalkyl, optionally substituted heteroaryl, cycloalkyloxy, cycloalkenyloxy, optionally substituted phenylcarbonylamino, optionally substituted heteroaralkyloxy, aminoalkyl, aminoalkoxy, alkoxyalkyl, alkoxyalkyloxy, methylenedioxy, haloalkoxyalkyl, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)$_n$-R$^a$ (where n is 0 to 2 and R$^a$ is alkyl, haloalkyl, hydroxyalkyl, alkoxyalkyl, optionally substituted phenyl, optionally substituted phenylalkyl, optionally substituted heteroaryl, or optionally substituted heteroaralkyl), -alkylene-NHSO$_2$—R$^b$ (where R$^b$ is alkyl, haloalkyl, optionally substituted phenyl, optionally substituted phenylalkyl, optionally substituted heteroaryl, or optionally substituted heteroaralkyl), -alkylene-NHCO-R$^c$ (where R$^c$ is alkyl, haloalkyl, optionally substituted phenyl, optionally substituted phenylalkyl, optionally substituted heteroaryl, or optionally substituted heteroaralkyl), or -(alkylene)$^{n1}$—CONR$^f$R$^g$ (where n1 is 0 or 1, R$^f$ is hydrogen, alkyl, or hydroxyalkyl and R$^g$ is hydrogen, alkyl, hydroxyalkyl, alkoxyalkyl, optionally substituted phenyl, optionally substituted phenylalkyl, optionally substituted heteroaryl, optionally substituted heteroaralkyl, or optionally substituted heterocycloalkylalkyl, or $R^f$ and $R^g$ together with the nitrogen atom to which they are attached from heterocycloalkyl) wherein the alkyl chain in haloalkoxyalkyl, optionally substituted phenyloxyalkyl, optionally substituted heteroaryloxyalkyl, or aminoalkyl is optionally substituted with one or two fluoro. Preferably, the substitutents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl.

"Heterocycloalkyloxy" means a —OR radical where R is heterocycloalkyl ring as defined above e.g., tetrahydrofuranyloxy, piperidinyloxy, oxy and the like.

"Heterocycloalkylalkyl" means a -(alkylene)-R radical where R is heterocycloalkyl ring as defined above e.g., tetrahydrofuranmethyl, piperidinylmethyl, morpholinylethyl, and the like.

"Heterocycloalkylalkyloxy" means a —OR radical where R is heterocycloalkylalkyl as defined above e.g., tetrahydrofuranmethyloxy, piperidinylmethyloxy, morpholinylethyloxy, and the like.

"Heteroaryl" means a monovalent monocyclic or bicyclic aromatic radical of 5 to 10 ring atoms containing one or more, preferably one, two, or three ring heteroatoms selected from N, O, or S, the remaining ring atoms being carbon. More specifically the term heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isooxazolyl, benzoxazolyl, benzothiophenyl, benzthiazolyl, quinolinyl, isoquinolinyl, benzopyranyl, and thiazolyl, and the like. Unless stated otherwise, the heteroaryl ring is optionally substituted with one, two, or three substituents independently selected from alkyl, alkoxy, halo, haloalkyl, haloalkoxy, amino, alkylamino, dialkylamino, hydroxy, hydroxyalkyl, hydroxyalkyloxy, hydroxyalkoxyalkyl, alkoxyalkyloxyalkyl, optionally substituted phenyl, cycloalkyloxy, cycloalkenyloxy, optionally substituted phenylcarbonylamino, optionally substituted heteroaryl, optionally substituted heteroaralkyloxy, aminoalkyl, aminoalkoxy, alkoxyalkyl, alkoxyalkyloxy, methylenedioxy, haloalkoxyalkyl, optionally substituted phenylalkyl, optionally substituted phenyloxy, optionally substituted phenylalkyloxy, optionally substituted phenyloxyalkyl, optionally substituted heteroaryloxyalkyl, optionally substituted heterocycloalkyloxyalkyl, optionally substituted heterocycloalkylalkyl, optionally substituted heterocycloalkylalkyloxy, optionally substituted heterocycloalkyloxy, -alkylene-S(O)n-$R^a$ (where n is 0 to 2 and $R^a$ is alkyl, hydroxyalkyl, alkoxyalkyl, haloalkyl, optionally substituted phenyl, optionally substituted phenylalkyl, optionally substituted heteroaryl, or optionally substituted heteroaralkyl), -alkylene-NHSO$^2$—$R^b$ (where $R^b$ is alkyl, haloalkyl, optionally substituted phenyl, optionally substituted phenylalkyl, optionally substituted heteroaryl, optionally substituted heteroaralkyl, or optionally substituted heterocycloalkyl), -alkylene-NHCO—$R^c$ (where $R^c$ is alkyl, haloalkyl, hydroxyl, optionally substituted phenyl, optionally substituted phenylalkyl, optionally substituted heteroaryl, optionally substituted heteroaralkyl, or optionally substituted heterocycloalkyl), -alkylene-CONR$^c$R$^d$ (where R$^c$ is as defined above and R$^d$ is hydrogen or alkyl), -alkylene-NR$^e$-alkylene CONR$^c$R$^d$ (where R$^c$ is as defined above and R$^d$ and R$^e$ are independently hydrogen or alkyl), -(alkylene)$_{n1}$—CONR$^f$R$^g$ (where n1 is 0 or 1, R$^f$ is hydrogen, alkyl, or hydroxyalkyl and R$^g$ is hydrogen, alkyl, hydroxyalkyl, alkoxyalkyl, optionally substituted phenyl, optionally substituted phenylalkyl, optionally substituted heteroaryl, optionally substituted heteroaralkyl, or optionally substituted heterocycloalkylalkyl, or R$^f$ and R$^g$ together with the nitrogen atom to which they are attached from heterocycloalkyl), or carboxyalkylaminoalkyl wherein the alkyl chain in haloalkoxyalkyl, optionally substituted phenyloxyalkyl, optionally substituted heteroaryloxyalkyl, or aminoalkyl is optionally substituted with one or two fluoro. Preferably, the substitutents are independently methoxy, methyl, ethyl, chloro, trifluoromethyl, fluoro, 2-methoxyethoxy, 2-(morpholin-4-yl)ethoxy, pyridin-3-ylmethoxy, 2-hydroxyethoxy, 2-(N,N-dimethylamino)ethoxy, methoxymethyl, phenoxymethyl, 2-morpholino-4-ylethyl, morpholino-4-ylmethyl, N,N-dimethylaminomethyl, i-propoxymethyl, or phenoxymethyl.

When the heteroaryl ring is divalent it has been referred to as heteroarylene in this application.

"Heteroarylamino" means a NHR radical where R is heteroaryl as defined above.

"Heteroaryloxy" means a —OR radical where R is heteroaryl as defined above.

"Heteroaralkyl" means a -(alkylene)-R radical where R is heteroaryl as defined above.

"Heteroaralkyloxy" means a —OR radical where R is heteroaralkyl as defined above.

"Methylenedioxy" means —CH$_2$—O—.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula (I) include compounds wherein a hydroxy, amidino, guanidino, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes N-oxide derivatives and protected derivatives of compounds of Formula (I). For example, when compounds of Formula (I) contain an oxidizable nitrogen atom, the nitrogen atom can be converted to an N-oxide by methods well known in the art. Also when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. 1981, the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid; lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated.

Certain compounds of Formula (I) can exist as tautomers and/or geometric isomers. All possible tautomers and cis and trans isomers, individual and mixtures thereof are within the scope of this invention. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth.

"Optionally substituted phenyl" means a phenyl ring optionally substituted with one, two, or three substituents independently selected from alkyl, halo, alkoxy, alkylthio, haloalkyl, haloalkoxy, heteroaryl (that is optionally substituted with one or two substituents independently selected from alkyl, halo, hydroxy, alkoxy, carboxy, amino, alkylamino, or dialkylamino), heterocycloalkyl (that is optionally substituted with one or two substituents independently selected from alkyl, halo, hydroxy, alkoxy, carboxy, amino, alkylamino, or dialkylamino), amino, alkylamino, dialkylamino, hydroxy, cyano, nitro, methylenedioxy, aminocarbonyl, acylamino, hydroxyalkyl, alkoxycarbonyl, aminoalkyl, or carboxy or optionally substituted with five fluorine atoms. When the phenyl is substituted it is referred herein as "substituted phenyl".

"Optionally substituted phenyloxy or phenoxy" means a —OR radical where R is optionally substituted phenyl as defined above e.g., phenoxy, chlorophenoxy, and the like.

"Optionally substituted phenylcarbonylamino" means a —NHCOR radical where R is optionally substituted phenyl as defined above e.g., benzoylamino, and the like.

"Optionally substituted phenylalkyl" means a -(alkylene)-R radical where R is optionally substituted phenyl as defined above e.g., benzyl, phenylethyl, and the like.

"Optionally substituted phenylalkyloxy" means a —O-(alkylene)-R radical where R is optionally substituted phenyl as defined above e.g., benzyloxy, phenylethyloxy, and the like.

"Optionally substituted phenyloxyalkyl or phenoxyalkyl" means a -(alkylene)-OR radical where R is optionally substituted phenyl as defined above e.g., phenoxymethyl, phenoxyethyl, and the like.

"Optionally substituted heteroaryl" means a monovalent monocyclic or bicyclic aromatic radical of 5 to 10 ring atoms containing one or more, preferably one, two, or three ring heteroatoms selected from N, O, or S, the remaining ring atoms being carbon. More specifically the term heteroaryl includes, but is not limited to, pyridyl, pyrrolyl, imidazolyl, thienyl, furanyl, indolyl, quinolyl, pyrazinyl, pyrimidinyl, pyridazinyl, oxazolyl, isooxazolyl, benzoxazolyl, benzothiophenyl, benzthiazolyl, quinolinyl, isoquinolinyl, benzopyranyl, thiazolyl, and the like that is optionally substituted with one, two, or three substituents independently selected from alkyl, halo, alkoxy, haloalkyl, haloalkoxy, amino, alkylamino, dialkylamino, hydroxy, cyano, nitro, aminocarbonyl, hydroxyalkyl, alkoxycarbonyl, aminoalkyl, optionally substituted phenyl, optionally substituted phenoxy, carboxy, or heteroaryl that is optionally substituted with alkyl, halo, hydroxy, alkoxy, carboxy, amino, alkylamino, or dialkylamino, heterocycloalkyl optionally substituted with one or two substitutents independently selected from alkyl, halo, hydroxy, alkoxy, amino, alkylamino or dialkylamino, heterocycloalkylalkyl optionally substituted with one or two substitutents independently selected from alkyl, halo, hydroxy, alkoxy, amino, alkylamino or dialkylamino, or heteroarylamino optionally substituted with one or two substitutents independently selected from alkyl, halo, hydroxy, alkoxy, amino, alkylamino or dialkylamino. When the heteroaryl is substituted it is referred herein as "substituted heteroaryl".

"Optionally substituted heteroaryloxy" means a —OR radical where R is optionally substituted heteroaryl as defined above e.g., furanyloxy, pyridinyloxy, and the like.

"Optionally substituted heteroaralkyloxy" means a —OR radical where R is optionally substituted heteroaralkyl ring as defined below.

"Optionally substituted heteroaryloxyalkyl" means a -(alkylene)-OR radical where R is optionally substituted heteroaryl ring as defined above.

"Optionally substituted heteroaralkyl" means a -(alkylene)-R radical where R is optionally substituted heteroaryl ring as defined above.

"Optionally substituted heterocycloalkyl" means a saturated or unsaturated monovalent cyclic group of 3 to 8 ring atoms in which one or two ring atoms are heteroatoms selected from N, O, or S(O)n, where n is an integer from 0 to 2, the remaining ring atoms being C. One or two ring carbon atoms can optionally be replaced by a —CO— group. More specifically the term heterocycloalkyl includes, but is not limited to, pyrrolidino, piperidino, morpholino, piperazino, tetrahydropyranyl, and thiomorpholino, and the derivatives thereof and N-oxide or a protected derivative thereof. The heterocycloalkyl is optionally fused to aryl and is optionally substituted with one, two, or three substituents independently selected from alkyl, cycloalkyl, halo, alkoxy, haloalkyl, haloalkoxy, amino, alkylamino, dialkylamino, hydroxy, cyano, nitro, optionally substituted phenylalkyl, optionally substituted heteroaralkyl, aminocarbonyl, hydroxyalkyl, alkoxycarbonyl, aminoalkyl, or carboxy. When the heterocycloalkyl is substituted it is referred herein as "substituted heterocycloalkyl".

"Optionally substituted heterocycloalkyloxy" means a —OR radical where R is optionally substituted heterocycloalkyl ring as defined above.

"Optionally substituted heterocycloalkylalkyl" means a -(alkylene)-R radical where R is optionally substituted heterocycloalkyl ring as defined above.

"Optionally substituted heterocycloalkylalkyloxy" means a —OR radical where R is optionally substituted heterocycloalkylalkyl ring as defined above.

"Optionally substituted heterocycloalkyloxyalkyl" means a -(alkylene)-OR radical where R is optionally substituted heterocycloalkyl as defined above e.g., piperidinyloxymethyl, pyrrolidinyloxyethyl, and the like.

"Optional" or "optionally" means that the subsequently described event or circumstance may but need not occur, and that the description includes instances where the event or circumstance occurs and instances in which it does not. For example, "heterocycloalkyl group optionally mono- or di-substituted with an alkyl group" means that the alkyl may but need not be present, and the description includes situations where the heterocycloalkyl group is mono- or disubstituted with an alkyl group and situations where the heterocycloalkyl group is not substituted with the alkyl group.

"Phenylene" means a divalent phenyl radical.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Treating" or "treatment" of a disease includes:

preventing the disease, i.e. causing the clinical symptoms of the disease not to develop in a mammal that may be exposed to or predisposed to the disease but does not yet experience or display symptoms of the disease;

inhibiting the disease, i.e., arresting or reducing the development of the disease or its clinical symptoms; or relieving the disease, i.e., causing regression of the disease or its clinical symptoms.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of Formula (I) are disclosed in Table I-IV below.

Compounds of Formula (I) where $R^1$ and $R^3$ are hydrogen, $Ar^1$ is phenyl and $Ar^2$ and Y are as defined in Table I below are:

TABLE I

[Structure: $Ar^2$—C($R^5$)=CH—CONH—Y—O—C$_6$H$_4$—C(=O)—NH—OH]

| Cpd # | $Ar^2$ | $R^5$ | Y |
|---|---|---|---|
| 1 | benzofuran-2-yl | pyrrolidin-1-ylmethyl | —CH$_2$—CH$_2$— |
| 2 | benzofuran-2-yl | 2-pyrrolidin-1-ylethoxymethyl | —CH$_2$—CH$_2$— |
| 3 | benzofuran-2-yl | 4-hydroxypiperidin-1-ylmethyl | —CH$_2$—CH$_2$— |
| 4 | benzofuran-2-yl | pyridin-3-yloxymethyl | —CH$_2$—CH$_2$— |
| 5 | benzofuran-2-yl | piperidin-1-ylmethyl | —CH$_2$—CH$_2$— |
| 6 | benzofuran-2-yl | N-benzyl-N-methylaminomethyl | —CH$_2$—CH$_2$— |
| 7 | benzofuran-2-yl | 4-trifluoromethylpiperidin-1-yl-methyl | —CH$_2$—CH$_2$— |
| 8 | benzofuran-2-yl | morpholin-4-ylmethyl | —CH$_2$—CH$_2$— |
| 9 | benzofuran-2-yl | N,N-dimethylaminomethyl | —CH$_2$—CH$_2$— |
| 10 | benzofuran-2-yl | N-methyl-N-(2-phenylethyl)-aminomethyl | —CH$_2$—CH$_2$— |
| 11 | benzofuran-2-yl | pyridin-2-yloxymethyl | —CH$_2$—CH$_2$— |
| 12 | benzofuran-2-yl | 2-methoxyethoxymethyl | —CH$_2$—CH$_2$— |
| 13 | benzofuran-2-yl | methylsulfonylaminomethyl | —CH$_2$—CH$_2$— |
| 14 | benzofuran-2-yl | azetidin-1-ylmethyl | —CH$_2$—CH$_2$— | and are named as:

4-[2-(3-benzofuran-2-yl-4-pyrrolidin-1-ylbut-2-enoylamino)ethoxy]-N-hydroxybenzamide;

4-{2-[3-benzofuran-2-yl-4-(2-pyrrolidin-1-ylethyloxy)but-2-enoylamino]ethoxy}-N-hydroxybenzamide;

4-{2-[3-benzofuran-2-yl-4-(4-hydroxypyrrolidin-1-yl)but-2-enoylamino)ethoxy]-N-hydroxybenzamide;

4-[2-(3-benzofuran-2-yl-4-pyridin-3-yloxybut-2-enoylamino)ethoxy]-N-hydroxybenzamide;

4-[2-(3-benzofuran-2-yl-4-piperidin-1-ylbut-2-enoylamino)ethoxy]-N-hydroxybenzamide;

4-{3-[3-benzofuran-2-yl-4-(benzylmethylamino)-but-2-enoylamino]-ethoxy}-N-hydroxy-benzamide 4-{2-[3-benzofuran-2-yl-4-(4-trifluoromethylpiperidin-1-yl)but-2-enoylamino)ethoxy]-N-hydroxybenzamide;

4-[2-(3-benzofuran-2-yl-4-morpholin-4-ylbut-2-enoylamino)ethoxy]-N-hydroxybenzamide;

4-{3-[3-benzofuran-2-yl-4-(dimethylamino)-but-2-enoylamino]-ethoxy}-N-hydroxy-benzamide;

4-{3-[3-benzofuran-2-yl-4-(methyl-2-phenylethylamino)-but-2-enoylamino]-ethoxy}-N-hydroxy-benzamide;

4-{2-[3-benzofuran-2-yl-4-(pyridin-2-yloxy)but-2-enoylamino]ethoxy}-N-hydroxybenzamide;

4-{2-[3-benzofuran-2-yl-4-(2-methoxyethyloxy)but-2-enoylamino]ethoxy}-N-hydroxybenzamide;

4-{3-[3-benzofuran-2-yl-4-(methylsulfonylamino)-but-2-enoylamino]-ethoxy}-N-hydroxy-benzamide; and 4-[2-(4-azetidin-1-y-3-benzofuran-2-ylbut-2-enoylamino)ethoxy]-N-hydroxybenzamide.

Preferred Embodiments

While the broadest definition of this invention is set forth in the Summary of the Invention, certain compounds of Formula (I) are preferred. For example:

(A). One preferred group of compound is that wherein X is —O—.

(B). Another preferred group of compounds is that wherein X is —O—, $R^1$ and $R^3$ are hydrogen, $Ar^1$ is phenylene and $Ar^2$ is heteroaryl.

(C). Yet another preferred group of compounds is that wherein X is —O—, $R^1$, $R^3$, and $R^4$ are hydrogen, $Ar^1$ is phenylene and $Ar^2$ is heteroaryl.

(D). Yet another preferred group of compounds is that wherein X is —O—, $R^1$, $R^3$, and $R^5$ are hydrogen, $Ar^1$ is phenylene and $Ar^2$ is heteroaryl.

(E). Yet another preferred group of compounds is that wherein X is —O—, $R^1$, $R^3$, and $R^4$ are hydrogen, $Ar^1$ is phenylene, $Ar^2$ is heteroaryl, and $R^5$ is —$CH_2NR^7R^8$ (where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl). More preferably, $R^5$ is N-methylaminomethyl, N,N-dimethylaminomethyl, N-benzyl-N-methylaminomethyl, or N-methyl-N-2-phenylethylaminomethyl.

(F). Yet another preferred group of compounds is that wherein X is —O—, $R^1$, $R^3$, and $R^4$ are hydrogen, $Ar^1$ is phenylene, $Ar^2$ is heteroaryl, and $R^5$ is —$CH_2$-heterocyloalkyl. Most preferably, $R^5$ is pyrrolidin-1-ylmethyl, azetidin-1-ylmethyl, piperidin-1-ylmethyl, 4-hydroxypiperidin-1-ylmethyl, or morpholin-4-ylmethyl.

(G). Yet another preferred group of compound is that wherein X is —O—, $R^1$, $R^3$, and $R^4$ are hydrogen, $Ar^1$ is phenylene, $Ar^2$ is heteroaryl, and $R^5$ is —$CH_2R^6$ where $R^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-S(O)$_n$—, hydroxyalkyl-S(O)$_n$—, —S(O)$_n$-aryl, aralkyl-S(O)$_n$—, —S(O)$_n$-heteroaryl, heteroaralkyl-S(O)$_n$—, —S(O)$_n$-heterocycloalkyl, heterocycloalkylalkyl-S(O)$_n$— (where n is 0, 1, or 2).

(H). Yet another preferred group of compounds is that wherein X is —O—, Y is —$CH(C_2H_5)CH_2$—, —$CH_2CH(CH_3)$— or ethylene, preferably ethylene, $R^1$, $R^3$, and $R^4$ are hydrogen, $Ar^1$ is phenylene, $Ar^2$ is heteroaryl, and $R^5$ is —$CH_2NR^7R^8$ (where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl). More preferably, $R^5$ is N-methylaminomethyl, N,N-dimethylaminomethyl, N-benzyl-N-methylaminomethyl, or N-methyl-N-2-phenylethylaminomethyl.

(I). Yet another preferred group of compounds is that wherein X is —O—, $R^1$, $R^3$, and $R^4$ are hydrogen, $Ar^1$ is phenylene, $Ar^2$ is heteroaryl, Y is —$CH(C_2H_5)CH_2$—, —$CH_2CH(CH_3)$— or ethylene, preferably ethylene, and $R^5$ is —$CH_2$-heterocyloalkyl. Most preferably, $R^5$ is pyrrolidin-1-ylmethyl, azetidin-1-ylmethyl, piperidin-1-ylmethyl, 4-hydroxypiperidin-1-ylmethyl, or morpholin-4-ylmethyl.

(J). Yet another preferred group of compounds is that wherein X is —O—, Y is —$CH(C_2H_5)CH_2$—, —$CH_2CH(CH_3)$— or ethylene, preferably ethylene, $R^1$, $R^3$, and $R^4$ are hydrogen, $Ar^1$ is phenylene, $Ar^2$ is heteroaryl, and $R^5$ is —$CH_2R^6$ where $R^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-S(O)$_n$—, hydroxyalkyl-S(O)$_n$—, —S(O)$_n$-aryl, aralkyl-S(O)$_n$—, —S(O)$_n$-heteroaryl, heteroaralkyl-S(O)$_n$—, —S(O)$_n$-heterocycloalkyl, heterocycloalkylalkyl-S(O)$_n$— (where n is 0, 1, or 2).

(K). Another preferred group of compounds is that wherein X is —O—, $R^1$ and $R^3$ are hydrogen, $Ar^1$ is phenylene and $Ar^2$ is aryl.

(L). Yet another preferred group of compounds is that wherein X is —O—, $R^1$, $R^3$, and $R^4$ are hydrogen, $Ar^1$ is phenylene and $Ar^2$ is aryl.

(M). Yet another preferred group of compounds is that wherein X is —O—, $R^1$, $R^3$, and $R^5$ are hydrogen, $Ar^1$ is phenylene and $Ar^2$ is aryl.

(N). Yet another preferred group of compounds is that wherein X is —O—, $R^1$, $R^3$, and $R^4$ are hydrogen, $Ar^1$ is phenylene, $Ar^2$ is aryl, and $R^5$ is —$CH_2NR^7R^8$ (where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl). More preferably, $R^5$ is N-methylaminomethyl, N,N-dimethylaminomethyl, N-benzyl-N-methylaminomethyl, or N-methyl-N-2-phenylethylaminomethyl.

(O). Yet another preferred group of compounds is that wherein X is —O—, $R^1$, $R^3$, and $R^4$ are hydrogen, $Ar^1$ is phenylene, $Ar^2$ is aryl, and $R^5$ is —$CH_2$-heterocyloalkyl. Most preferably, $R^5$ is pyrrolidin-1-ylmethyl, azetidin-1-ylmethyl, piperidin-1-ylmethyl, 4-hydroxypiperidin-1-ylmethyl, or morpholin-4-ylmethyl.

(P). Yet another preferred group of compounds is that wherein X is —O—, $R^1$, $R^3$, and $R^4$ are hydrogen, $Ar^1$ is phenylene, $Ar^2$ is aryl, and $R^5$ is —$CH_2R^6$ where $R^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-S(O)$_n$—, hydroxyalkyl-S(O)$_n$—, —S(O)$_n$-aryl, aralkyl-S(O)$_n$—, —S(O)$_n$-heteroaryl, heteroaralkyl-S(O)$_n$—, —S(O)$_n$-heterocycloalkyl, heterocycloalkylalkyl-S(O)$_n$— (where n is 0, 1, or 2).

(Q). Yet another preferred group of compounds is that wherein X is —O—, Y is —$CH(C_2H_5)CH_2$—, —$CH_2CH(CH_3)$— or ethylene, preferably ethylene, $R^1$, $R^3$, and $R^4$ are hydrogen, $Ar^1$ is phenylene, $Ar^2$ is aryl, and $R^5$ is —$CH_2NR^7R^8$ (where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl). More preferably, $R^5$ is N-methylaminomethyl, N,N-dimethylaminomethyl, N-benzyl-N-methylaminomethyl, or N-methyl-N-2-phenylethylaminomethyl.

(R). Yet another preferred group of compounds is that wherein X is —O—, Y is —$CH(C_2H_5)CH_2$—, —$CH_2CH(CH_3)$— or ethylene, preferably ethylene, $R^1$, $R^3$, and $R^4$ are hydrogen, $Ar^1$ is phenylene, $Ar^2$ is aryl, and $R^5$ is —$CH_2$-heterocyloalkyl. Most preferably, $R^5$ is pyrrolidin-1-ylmethyl, azetidin-1-ylmethyl, piperidin-1-ylmethyl, 4-hydroxypiperidin-1-ylmethyl, or morpholin-4-ylmethyl.

(S). Yet another preferred group of compounds is that wherein X is —O—, Y is ethylene, $R^1$, $R^3$, and $R^4$ are hydrogen, $Ar^1$ is phenylene, $Ar^2$ is aryl, Y is —$CH(C_2H_5)CH_2$—, —$CH_2CH(CH_3)$— or ethylene, preferably ethylene, and $R^5$ is —$CH_2R^6$ where $R^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-S(O)$_n$—, hydroxyalkyl-S(O)$_n$—, —S(O)$_n$-aryl, aralkyl-S(O)$_n$—, —S(O)$_n$-heteroaryl, heteroaralkyl-S(O)$_n$—, —S(O)$_n$-heterocycloalkyl, heterocycloalkylalkyl-S(O)$_n$— (where n is 0, 1, or 2).

Within groups (A)-(J), a more preferred group of compounds is that wherein the —CONHOH and X groups are at the 1 and 4 position of the phenylene ring and $Ar^2$ is heteroaryl optionally substituted with one or two independently selected from alkyl, halo, haloalkyl, alkoxy, alkoxyalkyl, hydroxyalkoxy, hydroxyalkoxyalkyl, alkoxyalkyloxy, alkoxyalkyloxyalkyl, aminoalkyl, aminoalkoxy, haloalkoxy, haloalkoxyalkyl, optionally substituted phenylalkyl, optionally substituted phenyloxyalkyl, optionally substituted heteroaryl, optionally substituted heteroaralkyloxy, optionally substituted heteroaryloxyalkyl, optionally substituted heterocycloalkylalkyl, optionally substituted heterocycloalkyloxy, optionally substituted heterocycloalkylalkyloxy, -alkylene-S(O)nR$^a$ (where n is 0 to 2 and R$^a$ is hydroxyalkyl or optionally substituted phenyl), -alkylene-NR$^e$-alkyleneCONR$_c$R$^d$ (where R$^c$ is hydroxyl and R$^d$ and R$^e$ are independently hydrogen or alkyl), or carboxyalkylaminoalkyl.

Preferably, Ar$^2$ is thiophen-2-yl, pyridin-3-yl, quinolin-6-yl, benzothiazol-2-yl, benzofuran-2-yl, benzothien-2-yl, furan-2-yl, 1H-benzimidazol-2-yl, 1H-pyrrol-2-yl, thiazol-2-yl, 1H-indol-2-yl, 1H-indol-5-yl, 1H-indol-3-yl, quinolin-3-yl, quinolin-8-yl, 1H-indazol-3-yl, 1H-benzotriazol-5-yl, isoquinolin-1-yl, isoquinolin-3-yl, quinoxalin-2-yl, quinolin-2-yl, 1H-benzimidazol-5-yl, quinolin-1-yl, pyridin-2-yl, quinolin-2-yl, furan-3-yl, or thiophen-3-yl, more preferably benzofuran-2-yl, or benzothien-2-yl which are optionally substituted with one or two substituents described immediately above.

Even more preferably Ar$^2$ is benzofuran-2-yl and is optionally mono-substituted at the 3-, 4- or 5-position or disubstitiued at the 4 and 7 positions, preferably the benzofuran-2-yl is optionally monosubstituted at the 3 or 5 position with a substituent described in second paragraph above. More preferably, the substituents are independently selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-ylmethoxy, 2-hydroxyethoxy, 2-N,N-dimethylaminoethoxy, methoxymethyl, 3-1-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1,2,4-triazin-1-yl-phenoxymethyl, 2-phenylethyl, pyrrolidin-1-ylmethyl, piperidin-1-ylmethyl, 4-trifluoromethylpiperidin-ylmethyl, 4-methylpiperazin-ylmethyl, 3,3,3-trifluoropropyloxymethyl, 4-fluorophenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, N-methyl-N-2-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylamino-methyl).

Even more preferably, Ar$^2$ is benzofuran-2-yl.

Even more preferably, Ar$^2$ is benzofuran-2-yl that is substituted at the 3-position with N,N-dimethylaminomethyl, N,N-diethylaminomethyl, 2-fluorophenoxymethyl, 3-fluorophenoxymethyl, 4-fluorophenoxymethyl, pyridin-4-yloxymethyl, 2,4,6-trifluorophenoxy-methyl, 2-oxopyridin-1-ylmethyl, 2,2,2-trifluoroethoxy-methyl, 4-imidazol-1-ylphenoxy-methyl, 4-[1,2,4-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethyl-piperidin-ylmethyl, 4-methylpiperazin-yl-methyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenylethyl)-, N-methyl-N-benzylaminomethyl, N-methyl-N-2-phenylethylaminomethyl, 3-hydroxypropylthiomethyl, 3-hydroxypropylsulfinyl-methyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylamino-methyl.

Even more preferably, Ar$^2$ is benzofuran-2-yl that is substituted at the 5-position with 1-cyclopropylpiperidin-4-yloxy, piperidin-4-yloxy, tetrahydropyran-4-yloxy, 2,2,2-trifluoroethoxy, 2-pyrrolidin-1-ylethyloxy, or 1-(2,2,2-trifluoroethyl)piperidin-4-yloxy.

Even more preferably, Ar$^2$ is 7-chloro-4-methylbenzofuran-2-yl, 4-methylbenzofuran-2-yl, 7-fluoro-4-methylbenzofuran-2-yl, or 7-fluoro-4-phenoxymethylbenzofuran-2-yl.

Within groups (K)—(S), a more preferred group of compounds is that wherein the —CONHOH and X groups are at the 1 and 4 position of the phenylene ring and Ar$^2$ is aryl optionally substituted with one or two substitutents independently selected from optionally substituted phenyl, alkyl, alkoxy, halo, optionally substituted heteroaryl, optionally substituted heteroaralkyloxy, optionally substituted hetercycloalkyl, optionally substituted phenylcarbonylamino, or methylenedioxy. More preferably, Ar$^2$ is phenyl, 4-biphenyl, 3-biphenyl, 4-tert-butylphenyl, 4-pyrrol-1-ylphenyl, 4-(pyridin-3-yl)phenyl, 4-(pyridin-2-yl)phenyl, 4-(benzoylamino)phenyl, 2,4-difluorophenyl, 3,4-methylenedioxyphenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-(thiophen-2-ylmethoxy)phenyl, 3-(thiophen-2-ylmethoxy)-phenyl, 2-biphenyl, naphth-1-yl, 2-pyrrol-1-ylphenyl, 4-fluoronaphth-2-yl, 3-MeO-naphth-2-yl, 2-MeO-naphth-1-yl, naphth-2-yl, 4-(2-pyridin-4-ylthiazol-2-yl)phenyl, 4-[2-(4-methylpiperazin-1-yl)thiazol-2-yl]-phenyl, 4-(2-pyridin-4-ylaminothiazol-2-yl)phenyl, 4-(4-methylpiperazin-1-yl)phenyl, 4-(4-hydroxypiperidin-1-yl)phenyl, 4-(4-morpholin-4-ylmethylthiazol-2-yl)phenyl, 4-[2-(4-methylpiperazin-1-ylmethyl)thiazol-2-yl]phenyl, 2-methoxynaphthyl, 3'-(3-hydroxypropyl)biphen-4-yl, 2'-(3-hydroxypropyl)biphen-4-yl, 2'-(3-hydroxypropyl)biphen-3-yl, or 4-[4-(2-morpholin-4-yl-ethyl)thiazol-2-yl]phenyl.

(T). Yet another more preferred group of compounds is that wherein Ar$^1$ is heteroarylene and Ar$^2$ is heteroarylene, preferably indol-2-yl, benzofuran-2-yl or benzothiophen-2-yl which are substituted with one or two substituents described in the definition section of this Application. Preferably, the substitutents are independently selected from alkyl, alkoxy, halo, haloalkyl, alkoxyalkyloxy, optionally substituted heterocycloalkylalkyloxy, optionally substituted heteroaralkyloxy, hydroxyalkoxy, aminoalkyloxy, alkoxyalkyloxy, alkoxyalkyl, optionally substituted phenyloxyalkyl, or optionally substituted heterocycloalkylalkyl. Preferably Ar$^1$ is a five membered heteroarylene ring containing one, two, or three heteroatoms independently selected from N, O or S, more preferably Ar$^1$ is thienyl or isoxazolyl where the hydroxamate and the X groups are located at the 5- and 3-position of the isoxazolyl ring, the oxygen atom in the ring being position 1 and Ar$^2$ is benzofuran-2-yl and benzothiophen-2-yl which are optionally substituted with methoxy, methyl, chloro, trifluoromethyl, fluoro, 2-methoxyethoxy, 2-morpholin-4-ylethoxy, pyridin-3-ylmethoxy, 2-hydroxyethoxy, 2-N,N-dimethylaminoethoxy, ethyl, methoxymethyl, phenoxymethyl, morpholin-4-ylmethyl, or dimethylaminomethyl and are located at the 3-position of the benzothiophen-2-yl and benzofuran-2-yl rings. Even more preferably, Ar$^1$ is benzofuran-2-yl or 3-phenoxymethylbenzofuran-2-yl. Within this group, a more preferred group of compounds is that wherein R$^1$, R$^3$, R$^4$ are hydrogen, X is —O—, Y is —CH(C$_2$H$_5$)CH$_2$—, —CH$_2$CH(CH$_3$)— or ethylene, preferably ethylene.

(U). Yet another more preferred group of compounds is that wherein Ar$^1$ is heteroarylene and Ar$^2$ is aryl. Preferably Ar$^1$ is five membered heteroarylene ring containing one, two, or three heteroatoms independently selected from N, O or S, more preferably Ar$^1$ is thienyl or isoxazolyl where the hydroxamate and the X groups are located at the 5- and 3-position of the isoxazolyl ring, the oxygen atom in the ring being position 1 and Ar$^2$ is aryl. Preferably Ar$^2$ is phenyl and is optionally substituted with one or two substitutents independently selected from alkoxy or optionally substituted phenyl. More preferably, methoxy, ethoxy, phenyl optionally substituted with ethoxy or methyl, methyl, tert-butyl, pyrrol-1-yl, cyclohexene-3-oxy, pyridin-3-yl, pyridin-2-yl, benzoylamino, fluoro, chloro, or thiophen-2-ylmethoxy. More preferably, Ar$^2$ is phenyl, 4-biphenyl, 3-biphenyl, 2-(2-ethoxyphenyl)phenyl, 3-methylbiphen-4-yl, 4-tert-butylphenyl, 4-pyrrol-1-ylphenyl, 4-(cyclohexene-3-oxy) phenyl, 4-(pyridin-2-yl)phenyl, 4-(pyridin-3-yl)-phenyl, 2,4-difluorophenyl, 3,4-dimethoxyphenyl, 3,5-dimethoxyphenyl, 3,4-difluorophenyl, 2,5-dimethylphenyl, 2,3-dichlorophenyl, 2,3-dimethylphenyl, 4-chloro-2-methoxyphenyl, 3-ethoxyphenyl, 4-methoxy-2-methylphenyl, 3-fluoro-4-methoxyphenyl, 2-thiophen-2-ylmethoxyphenyl, 3-thiophen-2-ylmethoxyphenyl, 2-biphenyl, or 2-pyrrol-1-ylphenyl. Within this group, a more preferred group of compounds is that wherein R$^1$, R$^3$, R$^4$ are hydrogen, X is —O—, Y is —CH(C$_2$H$_5$)CH$_2$—, —CH$_2$CH(CH$_3$)— or ethylene, preferably ethylene.

Within the above preferred, more preferred, and even more preferred group (T) and (U) above, particularly preferred group of compounds is that wherein R$^4$ is hydrogen and R$^5$ is —CH$_2$NR$^7$R$^8$ (where R$^7$ is hydrogen or alkyl and R$^8$ is alkyl, hydroxyalkyl, alkoxyalkyl, aryl, aralkyl, heteroaryl, heteroaralkyl, heterocycloalkyl, or heterocycloalkylalkyl). More preferably, N-methylaminomethyl, N,N-dimethylaminomethyl, N-benzyl-N-methylaminomethyl, or N-methyl-N-2-phenylethylaminomethyl.

Within the above preferred, more preferred, and even more preferred group (T) and (U) above, particularly preferred group of compounds is that wherein R$^4$ is hydrogen and R$^5$ is —CH$_2$-heterocyloalkyl. Most preferably, pyrrolidin-1-ylmethyl, azetidin-1-ylmethyl, piperidin-1-ylmethyl, 4-hydroxypiperidin-1-ylmethyl, or morpholin-4-ylmethyl.

Within the above preferred, more preferred, and even more preferred group (T) and (U) above, particularly preferred group of compounds is that wherein R$^4$ is hydrogen and R$^5$ is —CH$_2$R$^6$ where R$^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-S(O)$_n$—, hydroxyalkyl-S(O)$_n$—, —S(O)$_n$-aryl, aralkyl-S(O)$_n$—, —S(O)$_n$-heteroaryl, heteroaralkyl-S(O)$_n$—, —S(O)$_n$-heterocycloalkyl, heterocycloalkylalkyl-S(O)$_n$— (where n is 0, 1, or 2).

(V). Another preferred group of compounds is that wherein R$^1$ and R$^3$ are hydrogen, X is —O—, Y is ethylene or n-propylene, preferably ethylene, R$^4$ is hydrogen, and R$^5$ is —CH$_2$NR$^7$R$^8$ (where R$^7$ is hydrogen or alkyl and R$^8$ is alkyl, hydroxyalkyl, alkoxyalkyl, aryl, aralkyl, heteroaryl, heteroaralkyl, heterocycloalkyl, or heterocycloalkylalkyl). More preferably, N-methylaminomethyl, N,N-dimethylaminomethyl, N-benzyl-N-methylaminomethyl, or N-methyl-N-2-phenylethylaminomethyl.

(W). Another preferred group of compounds is that wherein R$^1$ and R$^3$ are hydrogen, X is —O—, Y is ethylene or n-propylene, preferably ethylene, R$^4$ is hydrogen, and R$^5$ is —CH$_2$ heterocyloalkyl. Most preferably, pyrrolidin-1-ylmethyl, azetidin-1-ylmethyl, piperidin-1-ylmethyl, 4-hydroxypiperidin-1-ylmethyl, or morpholin-4-ylmethyl.

Reference to the preferred embodiments set forth above is meant to include all combinations of particular and preferred groups unless stated otherwise.

General Synthesis

Compounds of this invention can be made by the methods depicted in the reaction scheme shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where X is —O— or —S(O)m-, R$^4$ is hydrogen and other groups are as described in the Summary of the Invention can be prepared by the procedure illustrated and described in Scheme A below.

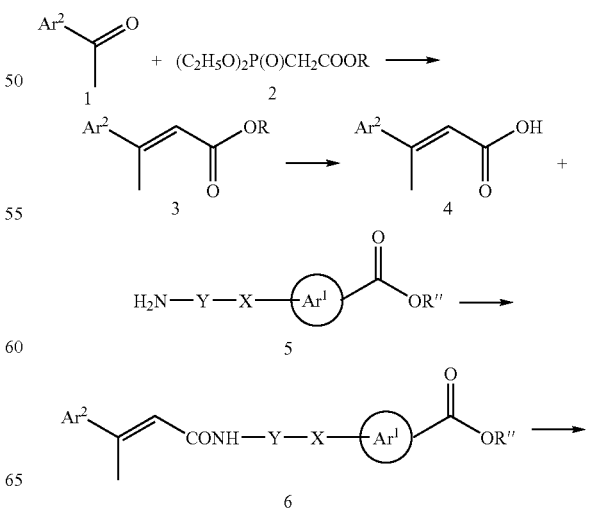

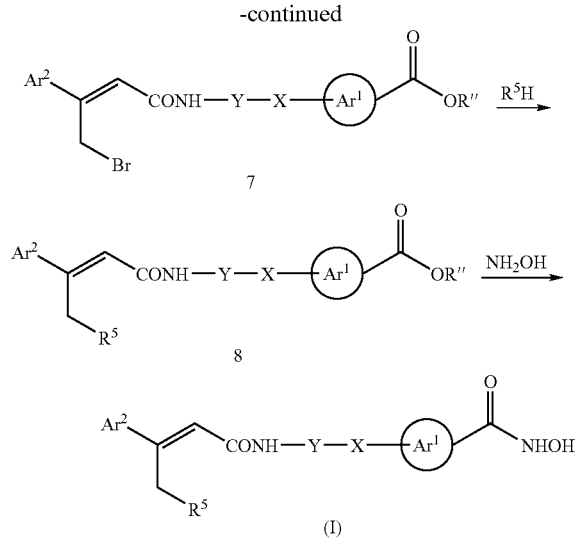

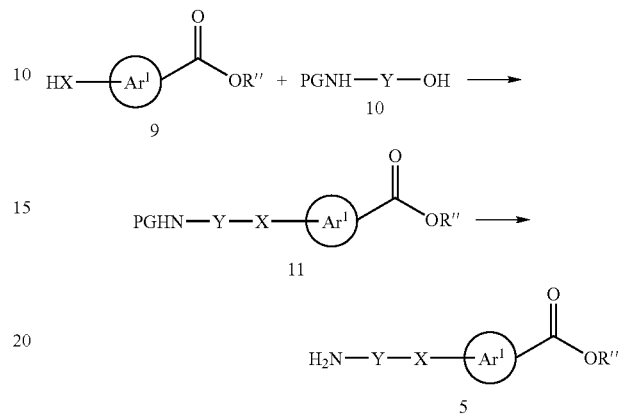

Reaction of a ketone of formula 1 where $Ar^2$ is as defined in the Summary of the Invention with a bis-ethoxyphosphonoacetate of formula 2 where R is an alkyl group such as methyl, ethyl, and the like, provides a compound of formula 3. The reaction is carried out in the presence of a base such as sodium hydride and the like, and in a suitable organic solvent such as tetrahydrofuran, and the like. Compounds of formula 1 such as benzofuran-2-yl methyl ketone, acetophenone, 2-acetylfuran, 2-acetylthiophene, 2-acetylpyrrole, 2-acetylthiazole, and 1-, 2-, or 3-acetylpyridine are commercially available. Others such as 5-methoxybenzofuran-2-yl methyl ketone can be prepared from 5-methoxybenzofuran 2-carboxylic acid by first converting the acid to a corresponding acid halide e.g., acid chloride using a suitable halogenating agent such as sulfonyl chloride, oxalyl halide, and the like under conditions known in the art. Treatment of the acid halide with methyl lithium then provide the desired ketone. 3-Phenoxymethyl-benzofuran-2-ylmethyl ketone can be prepared from 3phenoxymethylbenzofuran-2-carboxylic acid (prepared from commercially available 3-methylbenzofuran-2-carboxylic acid by first converting it to 2-bromomethylbenzofuran-2-carboxylic acid by brominating it with N-bromosuccinimide under conditions well known in the art, followed by reaction with phenol) as described above.

Removal of the alkyl protecting group in 3 under basic hydrolysis reaction condition provides the corresponding free acid compound of formula 4. Reaction of 4 with an amino compound of formula 5 where X is —O— or —S—, R" is alkyl, and Y is alkylene provides a compound of formula 6. The reaction is carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC. HCl), or 1,3-dicyclohexylcarbodiimide (DCC), optionally in the presence of 1-hydroxybenzotriazole hydrate (HOBT. H$_2$O), and a base such as N,N-diisopropylethylamine, triethylamine, N-methylmorpholine, and the like. The reaction is typically carried out at 20 to 30° C., preferably at about 25° C., and requires 2 to 24 hours to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. Compounds of formula 5 can be prepared as illustrated and described below.

Reaction of an ester compound of formula 9 where R" is alkyl, X is —O— or —S— and $Ar^1$ is as defined in the Summary of the Invention with an N-protected aminoalcohol of formula 10 where PG is a suitable amino protecting group provides a compound of formula 11. The reaction is carried out in the presence of triphenylphosphine and diisopropyl azodicarboxylate in a suitable organic solvent such as tetrahydrofuran, and the like. Compounds of formula 9 such as methyl 4-hydroxybenzoate and methyl 3-hydroxyisoxazole-5-carboxylate are commercially available. Compounds of formula 10 can be prepared from commercially available aminoalcohols by reacting the aminoalcohol with a suitable amino protecting group such as benzyloxycarbonyl, tert-butoxycarbonyl and the like under reaction conditions well known in the art. A detailed description of suitable amino protecting groups and reaction conditions for their preparation can be found in T. W. Greene, *Protecting Groups in Organic Synthesis*, John Wiley & Sons, Inc. 1999 the teaching of which is incorporated herein by reference in its entirety. Aminoalcohols such as 2-ethanolamine, 2-amino-1-propanol, 2-methylaminoethanol, 2-amino-2-methyl-1-propanol, 2-amino-1-propanol, 4-amino-2-butanol, and 1-amino-2-butanol are commercially available. Alternatively, compounds of formula 10 can be prepared from commercially available aminoacids such as glycine, alanine, and the like by protecting the amino group with a suitable protecting group followed by reduction of the acid group to the hydroxy group with a suitable reducing agent under conditions well known in the art.

Removal of the amino protecting group then provides a compound of formula 5. The reaction conditions employed for removal of the amino protecting group depends on the nature of the protecting group. For example, if the protecting group is tert-butoxycarbonyl, it is removed under acid reaction conditions. Suitable acids are trifluoroacetic acid, hydrochloric acid, and the like. If the protecting group is benzyl or benzyloxycarbonyl, it is removed under catalytic hydrogenation reaction conditions. Suitable catalyst are palladium based catalysts and others known in the art. Other suitable reaction conditions for their removal can be found in T. W. Greene, *Protecting Groups in Organic Synthesis*, John Wiley & Sons, Inc. 1999. The reaction is carried out in an inert organic solvent methylene chloride, tetrahydrofuran, dioxane, and the like. Compound 5 where X is —S— can be oxidized to give a corresponding compound of formula 5 where X is —SO$_2$— using an oxidizing agent such as Oxone®.

Bromination of 6 with a suitable brominating agent such as N-bromosuccinimide in the presence AIBN and in a suitable halogenated organic solvent such as carbon tetrachloride, chlorobenzene, and the like provides a compound of formula 7. Treatment of 7 with a compound of formula R$^5$H where R$^5$ is as defined in the Summary of the Invention provides a compound of formula 8. The reaction conditions utilized depend on the nature of the R$^5$ group. If R$^5$ is alkoxyalkyloxy, aryloxy, aralkyloxy, heteroaryloxy, heteroaralkyloxy, heterocycloalkyloxy, heterocycloalkylalkyloxy, alkoxyalkyl-S—, hydroxyalkyl-S—, —S-aryl, aralkyl-S—, —S-heteroaryl, heteroaralkyl-S—, —S-heterocycloalkyl, heterocycloalkylalkyl-S—, or —NR$^7$R$^8$ the reaction is carried out with the corresponding alcohol, thiol, or amine in the presence of a suitable base such as cesium carbonate, potassium carbonate, and the like, optionally in the presence of tetrabutylammonium iodide (when R$^5$ is alcohol) and in a suitable organic solvent such as dimethylformamide, tetrahydrofuran, and the like. Alternatively, compounds of formula 7 where R$^6$ is —NR$^7$R$^8$ or —NR$^9$SO$_2$R$^{10}$ can be prepared by converting the bromo group to an azido group by reacting 7 with sodium azide. Reduction of the azido group to an amino group, followed by reaction with an alkylating agent or sulfonylating agent under conditions described above then provides compounds of 8 where R$^6$ is —NR$^7$R$^8$ or —NR$^9$SO$_2$R$^{10}$ where R$^7$-R$^{10}$ are as defined in the Summary of the Invention. The groups present on the Ar$^1$ and/or Ar$^2$ ring can also be modified, if desired, prior to converting compound 8 to a compound of Formula (I). For example, compound 8 where Ar$^2$ is substituted with an alkoxy group can be dealkylated to give a corresponding compound of formula 8 where Ar$^2$ is substituted with hydroxy which can then be alkylated or arylated under conditions well known in the art.

Compound 8 is converted to a compound of Formula (I) by reacting it with aqueous hydroxylamine in the presence of a base such as sodium hydroxide and a mixture of organic solvents such as tetrahydrofuran and methanol. Other methods of preparing compounds of Formula (I) from compound 8 are analogous to the methods disclosed in U.S. Pat. No. 5,998,412, the disclosure of which is incorporated herein by reference in its entirety.

Compounds of Formula (I) where X is —O— or —S(O)m-, R$^5$ is hydrogen and other groups are as described in the Summary of the Invention can be prepared by the procedure illustrated and described in Scheme B below.

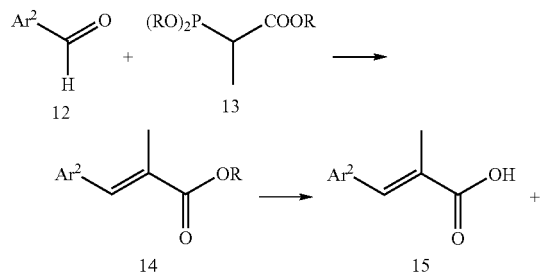

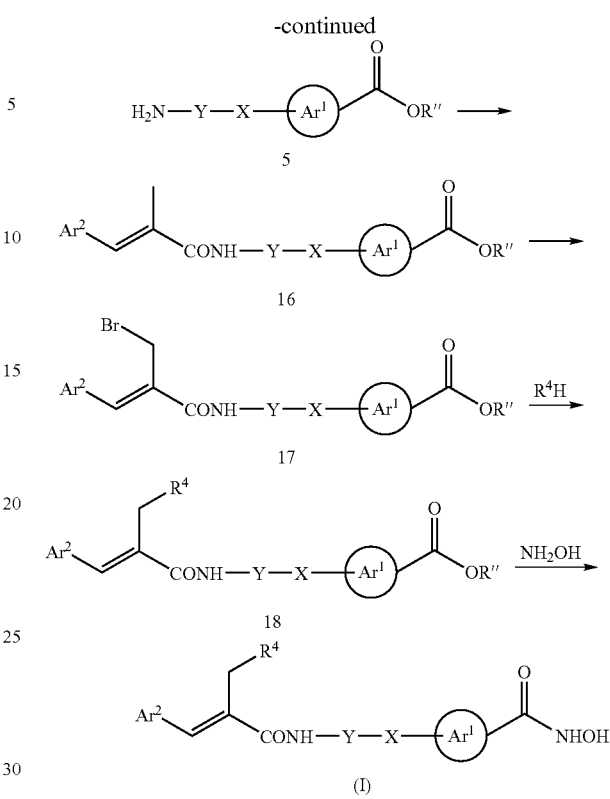

Reaction of an aldehyde 12 where Ar$^2$ is a defined in the Summary of the Invention with a phosphonate ester compound of formula 13 where R is alkyl provides a compound of formula 14. The reaction is carried out in the presence of a base or sodium hydride in an aprotic solvent such as tetrahydrofuran, diethyl ether, and the like. Compounds of formula 12 and 13 are commercially available or they can be prepared by methods well known in the art. Compounds of formula 12 such as 2-benzofuran carboxaldehyde, 2-furaldehyde, 2-thiophene carboxaldehyde, benzaldehyde, and 2-benzothiophene carboxaldehyde are commercially available. Compound 12 can also be synthesized from a carboxylic acid of formula A$^2$COOH by first converteing it to a Weinreb amide and reducing the Weinreb amide with a suitable reducing agent such as lithium aluminum hydride. Phosphonates of formula 13 can be prepared by reacting the corresponding halide with trialkyl phosphate at a high temperature. Compound 14 is then converted to a compound of Formula (I) as described in Scheme A above.

Utility

The compounds of this invention are inhibitors of histone deacetylase enzymes and are therefore useful in the treatment of proliferative diseases such as cancer such as lung, colon, AML, MML, skin, breast, ovarian, prostate, liver, brain and skin, psoriasis, fibroproliferative disorder such as liver fibrosis, smooth muscle proliferative disorder such as atherosclerosis and restenosis, inflammatory diseases such as arthritis, diseases involving angiogenesis such as cancer, diabetic retinopathy, haematopoietic disorder such as anaemia, fungal, parasitic and bacterial infections, viral infection, autoimmune diseases such as arthritis, multiple sclerosis, lupus, allergies, asthma, allergic rhinitis, and organ transplant, and bipolar disorders. Additionally, the compounds of the present invention are useful in the treatment of hepatitis C infection.

Testing

The ability of the compounds of this invention to inhibit histone deacetylase enzymes can be tested in vitro and in vivo assays described in biological assays Example 1 and 2 below.

Administration and Pharmaceutical Compositions

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.1-50 mg per kilogram body weight of the recipient per day; preferably about 0.5-20 mg/kg/day. Thus, for administration to a 70 kg person, the dosage range would most preferably be about 35 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral or parenteral using a convenient daily dosage regimen, which can be adjusted according to the degree of affliction. Oral compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18$^{th}$ ed., 1990).

The amount of the compound in a formulation can vary within the full range employed by those skilled in the art. Typically, the formulation will contain, on a weight percent (wt %) basis, from about 0.01-99.99 wt % of a compound of Formula (I) based on the total formulation, with the balance being one or more suitable pharmaceutical excipients. Preferably, the compound is present at a level of about 1-80 wt %. Representative pharmaceutical formulations containing a compound of Formula (I) are described below.

As stated previously, the compounds of this invention can be administered in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, DNA methyl tranferase inhibitors, and other angiogenesis inhibitors. The compound of the present invention compounds are particularly useful when administered in combination with radiation therapy. Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-(o-chloroacetylcarbonyl)-fumagillol, thalidomide, angiostatin, troponin-1, and an antibody to VEGF.

Preferred estrogen receptor modulators are tamoxifen and raloxifene.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)colchic(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)-amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)-ethylamino]-7-methoxy-9-oxo-9H-thioxanthen-4-ylmethyl] formamide, N-(2-(dimethylamino)-ethyl)acridine-4-carboxamide, 6-[[2-(dimethylamino)ethyl]amino]-3-hydroxy-7H-indeno[2, 1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetra cyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein. It has been reported that (*Int. J. Cancer,* 20;97(6): 746-50, 2002) combination therapy with lovastatin, a HMG-CoA reductase inhibitor, and butyrate, an inducer of apoptosis in the Lewis lung carcinoma model in mice showed potentiating antitumor effects Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the methods of the present invention are described at page 87 of M. Yalpani, "Cholesterol Lowering Drugs", Chemistry & Industry, pp. 85-89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and colchicine the use of such salts, esters, open-acid and lactone forms is included within the scope of this invention.

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin.

Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium hydroxy, camsylate, carbonate, chloride, clavulanate, citrate, dihydrochloride, hydroxy, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chloro phenyl)-1-methyl-2(1H)-quinolinone, (−)-6-[amino(4-chlorophenyl)(1-methyl-1H-imidazol-5-yl) methyl]-4-(3-chloro phenyl)-1-methyl-2(1H)-quinolinone, (+)-6-[amino(4-chlorophenyl)(1-methyl-1H-imidazol-5-yl) methyl]-4-(3-chloro phenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)-methyl]-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl) benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2'] bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H, 17H-18,21-ethano-6,10: 12,16-dimetheno-22H-imidazo[3,4-h][1,8,11,14]oxatriazacyclo-eicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *J. of Cancer*, Vol. 35, No. 9, pp. 1394-1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HB Y097, lamivudine, nevirapine, AZT, 3TC, ddC, and ddI. It has been reported (*Nat. Med.;* 8(3):225-32, 2002) that HIV protease inhibitors, such as indinavir or saquinavir, have potent anti-angiogenic activities and promote regression of Kaposi sarcoma "Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin., Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell, Vol.* 93, p. 705 (1998); *Intl. J. Mol. Med.*, Vol. 2, p. 715 (1998); *J. Biol. Chem.*, Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, Nature Biotechnology, Vol.

17, pp. 963-968 (October 1999); Kim et al., *Nature,* 362, 841-844 (1993); WO 00/44777; and WO 00/61186).

As described above, the combinations with NSAID's are directed to the use of NSAID's which are potent COX-2 inhibiting agents.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinaline, 5-amino-1-[[3,5-dichloro-4-(4-chlorobenzoyl)phenyl]-methyl]-1H-1,2,3-triazole-4-carboxamide, CM101, squalamine, combretastatin, RP14610, NX31838, sulfated mannopentose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_3$, and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethyl-phenyl)-5-methylisoxazol-4-carboxamide, 3-[(2,4-dimethylpyrrol-5-yl)methylidenyl)-indolin-2-one, 17-(allylamino)-17-demethoxygeldanamycin, 4-(3-chloro-4-fluorophenyl-amino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo [2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, SU11248, ST1571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, Platelets 10, 285-292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

"DNA methyltransferase inhibitor" refers to compounds which inhibit the methylation of the DNA base cytosine at the C-5 position of that base by the DNA methyltransferase enzyme. Examples of such DNA methyltransferase inhibitor include compounds disclosed in U.S. Pat. Nos. 6,329,412 and 6,268,137. Specific DNA methyltransferase inhibitors include 5-azacytosine and zebularine®.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

The term administration and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the farnesyl-protein transferase inhibitors disclosed in U.S. Pat. No. 6,313,138 and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®, epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as colchicines, etoposide, etoposide phosphate or teniposide, vinblastine, vincristine, leurosidine, vindesine, leurosine, and the like. Other useful antineoplastic agents include estramustine, cisplatin, carboplatin, cyclophosphamide, bleomycin, tamoxifen, ifosamide, melphalan, hexamethyl melamine, thiotepa, cytarabine, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. The preferred class of antineoplastic agents is the taxanes and the preferred antineoplastic agent is paclitaxel.

Radiation therapy, including x-rays or gamma rays that are delivered from either an externally applied beam or by implantation of tiny radioactive sources, may also be used in combination with the compounds of this invention alone to treat cancer.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of 4-[2-(4-azetidin-1-yl-3-benzofuran-2-yl-but-2-enoylamino)ethoxy]-N-hydroxybenzamide hydrochloride

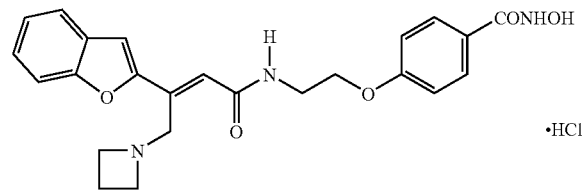

Step 1

A suspension of 60% NaH in paraffin oil (0.250 g, 6.1 mmol, 1.1 eq.) which was washed with hexane, was added to a solution of triethylphosphonoacetate (1.12 ml, 5.6 mmol) in THF (15 ml) and the reaction mixture was stirred for 1 h. A solution of benzofuran-2-yl methyl ketone (1.0 g, 5.6 mmol) in THF (5 ml) was added to the vigorously stirred mixture at such a rate as to maintain the temperature below 10° C. After 1 h, the reaction mixture was added to water (40 ml) and extracted with ether. The organic extracts were washed with saturated solution of NaCl and dried over sodium sulfate. After concentration, the crude product was purified on silica gel column, using ethyl acetate/hexane (2/8) as eluent. A mixture of isomers E/Z isomers (410 mg) was obtained in a 3:2 ratio, respectively. The resulting mixture was crystallized from ether/hexanes to obtain trans 3-benzofuran-2-ylbut-2-enoic acid ethyl ester as a white solid (230 mg).

Step 2

To a solution of trans 3-benzofuran-2-yl-but-2-enoic acid ethyl ester (0.760 mg, 3.52 mmol) in methanol (8 ml), a solution of NaOH in water (3 ml) was added. The reaction mixture was stirred at r.t. overnight. The pH was adjusted to about 3 by adding 1 N HCl. Methanol was evaporated under vacuum and the solid was filtered, washed with fresh water and left under vacuum, overnight to give trans 3-benzofuran-2-yl-but-2-enoic acid (560 mg).

Step 3

To a solution of 2-aminoethanol (3.1 g, 50 mmol) in THF (ml) was added tert-butyloxycarbonyl anhydride (10.9 g, 50 mmol) in THF (150 ml). The reaction mixture was stirred for 3 h, then diluted with ethyl acetate (~150 ml), washed with 0.5 M aqueous HCl, and washed with brine (~150 ml). The organic layer was dried (MgSO$_4$), filtered and concentrated in vacuo to give 2-N-Boc-aminoethanol which was directly used in the next step.

Step 4

To a solution of triphenylphosphine (17.7 g, 67.5 mmol) in anhydrous THF (135 ml) was added DIAD (13.6 g, 67.5 mmol). The solution was stirred until a white precipitate was formed (2 to 10 min). After additional 60 min, a solution of 2-N-Boc amino-ethanol (7.2 g, 45 mmol) and methyl 4-hydroxybenzoate (6.8 g, 45 mmol) in THF (~25 ml) was added and stirring was continued for 5 h. The reaction mixture was concentrated in vacuo and purified by flash chromatography to give methyl 4-(2-N-Boc aminoethoxy)benzoate. Alternatively, the crude material can directly be used in the next step.

Step 5

To a solution of crude methyl 4-(2-N-Boc aminoethoxy) benzoate in methanol (~20 ml) was added 4M HCl/dioxane (180 ml). After stirring for ~3 h diethyl ether (~300 ml) was added providing a white precipitate. The solid was collected, suspended in ethyl acetate and stirred for 15-20 min. The solid was collected again and dried under high vacuo providing methyl 4-(2-aminoethoxy)benzoate hydrochloride (6.3 g, 60% over 2 steps).

Step 6

To a solution of trans 3-benzofuran-2-yl-but-2-enoic acid (2.5 g, 12.3 mmol) and methyl 4-(2-aminoethoxy)benzoate (2.86 g, 12.3 mmol) in DMF (20 ml), HATU (4.71 g, 12.4 mmol) and DIPEA (6.42 ml, 36.9 mmol) were added. The reaction mixture was stirred at rt., overnight. The reaction mixture was diluted with ethyl acetate (150 ml) and washed with water (50 ml), sat NaHCO$_3$ (100 ml), and brine (100 ml). After drying over sodium sulfate, the solvent was removed under vacuum and the crude was purified by flash chromatography, using ethyl acetate/hexanes (3/7 and 1/1) to provide trans 4-[2-(3-benzofuran-2-ylbut-2-enoyl-amino) ethoxy]benzoic acid methyl ester as a white solid (4.11 g).

Step 7

A solution of 4-[2-(3-benzofuran-2-ylbut-2-enoylamino) ethoxy]benzoic acid methyl ester (2.0 g, 5.3 mmol), N-bromosuccinimide (0.938 g, 5.3 mmol) and AIBN (87 mg, 0.53 mmol) in carbon tetrachloride (100 ml) was heated at 80° C. for 4 h. The reaction mixture was diluted with chloroform (100 ml) and the organic solution was washed with water and brine. After drying over sodium sulfate, the solvents were evaporated under vacuum and the crude was crystallized from a mixture of ethyl acetate/hexanes to give of trans 4-[2-(3-benzofuran-2-yl-4-bromobut-2-enoylamino)ethoxy] benzoic acid methyl ester (1.15 g).

Step 8

To a solution of 4-[2-(3-benzofuran-2-yl-4-bromobut-2-enoylamino)ethoxy]benzoic acid methyl ester (300 mg, 0.654 mmol)) in dry DMF (4 ml), potassium carbonate (180 mg, 1.31 mmol) and azetidine hydrochloride (41 mg, 0.719 mmol) were added. The reaction mixture was stirred for 4 h at 50° C. The reaction mixture was diluted with ethyl acetate and the resulting suspension was washed with water and brine. After drying the organic phase over sodium sulfate, the solvent was removed under vacuum and the residue was purified by flash chromatography, using mixture of DCM/ MeOH (9.5/0.5) as eluent to give 4-[2-(4-azetidin-1-yl-3-benzofuran-2-yl-but-2-enoylamino)ethoxy]benzoic acid methyl ester.

Step 9

To a solution of 4-[2-(4-azetidin-1-yl-3-benzofuran-2-yl-but-2-enoylamino)ethoxy]-benzoic acid methyl ester (158 mg, 0.362 mmol) in THF (4 ml), a solution of hydroxylamine in 50% water (2.78 ml) and 1N NaOH (0.1 ml) were added. Methanol was added dropwise until a homogeneous solution was obtained. The reaction mixture was stirred overnight at rt. After cooling the mixture at 0° C., 6 N HCl was added until pH 7 was reached. The solid was separated by filtration and the crude solid purified by HPLC to give the title compound (25 mg) as a white solid.

¹HNMR (DMSO-d₆): δ 9.80 (1H, bs), 9.11 (1H, t), 8.89 (1H, s), 7.73 (4H, m), 7.58 (1H, d), 7.42 (1H, m), 7.31 (1H, m), 7.01 (1H, s), 7.00 (2H, d), 4.68 (2H, d), 4.14 (6H, m), 3.61 (2H, q), 2.35 (2H, m). LC/MS, M+1: 436.3.

Following the procedure in Example 1 above, the following compounds of the invention were synthesized.

Cpd 1:
¹HNMR (DMSO-d₆): δ 9.15 (1H, t), 8.88 (1H, s), 7.70 (2H, d), 7.64 (1H, d), 7.53 (1H, d), 7.33 (2H, m), 7.23 (1H, t), 6.98 (1H, d), 6.69 (1H, s), 4.10 (2H, t), 3.91 (2H, s), 3.55 (2H, q), 2.49 (4H, m), 1.60 (4H, m). LC/MS: M+1: 450.1.

Cpd 3:
¹HNMR (DMSO-d₆): δ 9.24 (1H, m), 8.90 (1H, bs), 7.71 (4H, m), 7.58 (1H, d), 7.42 (1H, t), 7.30 (1H, t), 7.10 (1H, d), 7.00 (2H, d), 5.05 (1H, bs), 4.56 (2H, m), 4.15 (2H, t), 3.92 (1H, s), 3.63 (2H, m), 3.35 (4H, m), 1.90 (2H, m), 1.70 (2H, m). LC/MS: M+1: 480.3.

Cpd 5:
¹H NMR (400 MHz, DMSO-d₆): δ1.7-1.8 (m, 1 H), 1.85-1.9 (m, 3 H), 1.9-1.95 (m, 2 H), 3.1-3.2 (m, 2 H), 3.4-3.6 (m, 2 H), 3.6-3.7 (q,m, 2 H), 4.15-4.25 (t, 2 H), 4.55-4.6 (m, 2 H), 7.0-7.1 (d, 2 H), 7.15 (s, 1 H), 7.3-7.4 (t, 1 H), 7.4-7.5 (t, 1 H), 7.6-7.7 (d, 1 H), 7.7 (s, 1 H), 7.75-7.8 (m, 4 H), 8.8-8.9 (m, 1 H), 10.1-10.2 (m,1 H). LC\MS: M+H⁺ (464.1).

Cpd 6:
¹H NMR (400 MHz, DMSO-d₆): δ 2.7-2.8 (m, 3 H), 3.6-3.7 (t,m, 2 H), 4.15-4.25 (t, 2 H), 4.4-4.5 (m, 2 H), 4.6-4.7 (m, 2 H), 4.55-4.6 (m, 2 H), 7.0-7.1 (d, 2 H), 7.15 (s,1 H), 7.3-7.4 (t, 1 H), 7.4-7.55 (m, 3 H), 7.55-7.65 (m, 3 H), 7.7 (s,1 H), 7.75-7.8 (m, 4 H), 9.15-9.2 (m, 1 H), 9.9-10.0 (m, 1 H). LC\MS: M+H⁺ (500).

Cpd 8:
¹H NMR (400 MHz, DMSO-d₆): δ3.2-3.4 (m, 2 H), 3.5-3.6 (q,m, 2 H), 3.6-3.7 (t,m, 2 H), 3.85-3.95 (m, 2 H), 4.15-4.25 (t, 2 H), 4.55-4.6 (m, 2 H), 7.0-7.1 (d, 2 H), 7.15 (s, 1 H), 7.2-7.3 (t,1 H), 7.3-7.4 (t, 1 H), 7.6-7.7 (m, 4 H), ), 9.15-9.2 (m, 1 H), 9.9-10.0 (m, 1 H). LC\MS: M+H⁺ (466.3).

Cpd 9:
LC\MS: M+1: 423.9, M−1: 422.3. ¹HNMR (DMSO-d₆): δ 2.87(s, 6H), 3.62(q, 2H), 4.15(t, 2H), 4.52(d, 2H), 6.99(d, 2H), 7.1(s, 1H), 7.32(t, 1H), 7.4(t, 1H), 7.58(d, 1H), 7.72(d, 4H), 9.26(s, 2H), 10.27(s, 1H).

Cpd 10:
¹H NMR (400 MHz, DMSO-d₆): δ 2.25-2.3 (s, 3H), 2.65-2.75 (m, 2 H), 2.75-2.85 (m, 2H), 3.9-3.95 (s, 2 H), 4.1-4.15 (t, 2 H), 6.75-6.8 (s, 1 H), 7.0-7.1 (d, 2 H), 7.1 (s, 1 H), 7.2-7.35 (m, 3 H), 7.35-7.4 (m, 2 H), 7.55-7.65 (dd, 3 H), 7.7-7.8 (m, 3 H), 7.75-7.8 (d,m, 4 H), 8.95-9.05 (m, 1 H). LC\MS: M+H⁺ (514.2).

Cpd 14:
¹HNMR (DMSO-d₆): δ 9.80 (1H, bs), 9.11 (1H, t), 8.89 (1H, s), 7.73 (4H, m), 7.58 (1H, d), 7.42 (1H, m), 7.31 (1H, m), 7.01 (1H, s), 7.00 (2H, d), 4.68 (2H, d), 4.14 (6H, m), 3.61 (2H, q), 2.35 (2H, m). LC/MS: M+1: 436.3.

Example 2

Synthesis of 4-{2-[3-benzofuran-2-yl-4-(2-pyrrolidin-1-ylethoxy)but-2-enoylamino]-ethoxy}-N-hydroxybenzamide hydrochloride

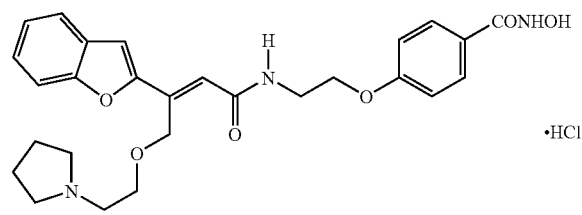

Step 1

To a solution of 4-[2-(3-benzofuran-2-yl-4-bromobut-2-enoylamino)ethoxy]benzoic acid methyl ester (300 mg, 0.654 mmol) in dry DMF (4 ml), cessium hydroxide monohydrate (121 mg, 0.72 mmol), tetrabutylammonium iodide (49 mg, 0.13 mmol) and 1-(2-hydroxy-ethyl)pyrrolidine (85 ul, 0.72 mmol) were added. The reaction mixture was stirred overnight at rt and then diluted with EA (20 ml) and washed with water and brine. After drying over sodium sulfate, the solvent was evaporated under vacuum and the crude was purified on preparative TLC, DCM/MeOH (9/1) to give 4-{2-[3-benzofuran-2-yl-4-(2-pyrrolidin-1-yl-ethoxy)but-2-enoylamino]ethoxy}benzoic acid methyl ester (0.94 mg) as an oil.

Step 2

To a solution of 4-{2-[3-benzofuran-2-yl-4-(2-pyrrolidin-1-ylethoxy)but-2-enoyl-amino]ethoxy}benzoic acid methyl ester (90 mg, 0.182 mmol) in THF (1 ml), a solution of hydroxylamine in 50% water (1 ml) and 1N NaOH (0.050 ul) were added. Methanol was added dropwise until a homogeneous solution was obtained and the reaction mixture was stirred overnight at rt. After cooling the mixture at 0° C., 6 N HCl was added until pH 7 was reached. The crude solid was filtered and purified by HPLC to give the title compound (17 mg) as white solid. LC/MS, M+1: 494.3; M−1: 492.2.

Following the procedure in Example 1 above, the following compounds of the invention were synthesized.

Cpd 4:
LC\MS: (M+1: 474.4, (M−1)⁻¹ 471.9

Cpd 11:
¹H NMR (400 MHz, DMSO-d₆): δ 3.6-3.7 (q,m 2 H), 4.15-4.25 (t, 2 H), 5.6-5.7 (s, 2 H), 6.2-6.3 (t,m, 1 H), 6.45-6.55 (d,1 H), 7.0-7.1 (m, 3 H), 7.25-7.3 (t, 1 H), 7.35-7.45 (m, 3 H), 7.55-7.6 (d,1 H), 7.65-7.7 (d,1 H), 7.7-7.8 (m, 3 H), 8.95-9.05 (m, 1 H). M+H⁺ (474.2).

Cpd 12:
LC\MS: M+1: 455.3, M−1: 453.3

Example 3

Synthesis of 4-[2-(3-benzofuran-2-yl-4-methanesulfonylaminobut-2-enoylamino)ethoxy]-N-hydroxybenzamide

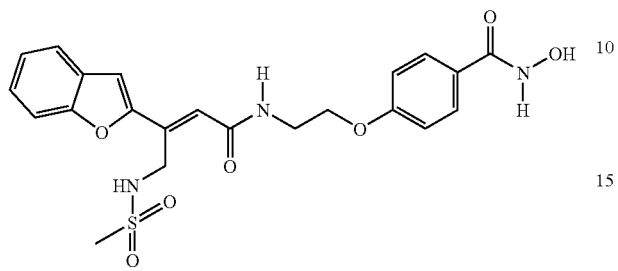

Step 1

To a solution of 4-[2-(3-benzofuran-2-yl-4-bromobut-2-enoylamino)ethoxy]benzoic acid methyl ester (0.60 g, 1.31 mmol) in DMF (5 ml), NaN$_3$ (93 mg, 1.4 mmol) was added. The reaction mixture was stirred for 5 h at rt and 18 h at 50° C. After diluting with ethyl acetate (50 ml), the reaction mixture was washed with water (20 ml) and brine (20 ml). The organic layer was dried over sodium sulfate and then evaporated to dryness. The crude was purified by flash chromatography to give 4-[2-(4-azido-3-benzofuran-2-yl-but-2-enoylamino)-ethoxy]benzoic acid methyl ester a white solid (478 mg).

Step 2

To a solution of 4-[2-(4-azido-3-benzofuran-2-ylbut-2-enoylamino)-ethoxy]benzoic acid methyl ester (0.47 g, 0.11 mmol) in THF (10 ml), TPP (0.439 g, 1.67 mmol) and water (0.040 ml, 2.22 mol) were added. The reaction mixture was stirred for 20 h at rt. After a formation of a solid was observed, another portion of water was added (0.040 ml, 2.22 mmol) and the reaction mixture was further stirred at 45° C. for 1.5 h. The reaction mixture was divided into half and methanesulfonyl chloride (0.047 ml, 0.6 mmol) and triethylamine (0.084 ml, 0.6 mmol) were added. After stirring for 16 h at rt., the reaction mixture was poured into water (15 ml) and the crude product extracted with ethyl acetate. The combined extracts were washed with brine and dried over sodium sulfate. After solvent evaporation, the residue was purified by column chromatography to give 4-[2-(3-benzofuran-2-yl-4-methanesulfonylamino-but-2-enoylamino)-ethoxy]-benzoic acid methyl ester as a white solid (70 mg which was then converted to the title compound as described in Example 1 above (23 mg).

$^1$HNMR (DMSO-d$_6$): δ9.00 (1H, bs), 8.77 (1H, t), 7.70 (3H, m), 7.54 (1H, d), 7.36 (1H, m), 7.31 (1H, s), 7.26 (1H, m), 7.18 (1H, t), 7.00 (2H, d), 6.79 (1H, s), 4.57 (2H, d), 4.11 (2H, t), 3.56 (2H, q), 2.95 (3H, s). LC/MS, M+1: 474.2. LC/MS, M+1: 474.2.

Example 4

Synthesis of acetyl-Gly-Ala-(N-acetyl-Lys)-AMC tert-Boc (N-Acetyl-Lys)-AMC (445 mg, 1 mmol, purchased from Bachem) was dissolved in 4 M HCL in dioxane to provide H-(N-acetyl-Lys)-AMC as a white solid. To a solution of H-(N-acetyl-Lys)-AMC in DMF (5 ml) was added Ac-Gly-Ala-OH (188 mg, 1 mmol) using PyBOP (520 mg, 1 mmol), HOBt (135 mg, 1 mmol), and NMM (0.296 ml, 2 mmol). The reaction mixture was stirred for 1 h and monitored by MS/LC for the presence of H-(N-acetyl-Lys)-AMC. Additional amounts of PyBOP (260 mg, 0.5 mmol), HOBt (70 mg, 0.5 mmol), and NMM (0.146 ml, 1 mmol) was added and the stirring was continued for additional 4 h after which the product was isolated in quantative yield.

Biological Examples

Example 1

Inhibition of HDAC In Vitro

The HDAC inhibitory activity of the compounds of this invention in vitro was determined as follows.

Measurements were performed in a reaction volume of 100 μL using 96-well assay plates. HDAC-1 (200 pM final concentration) in reaction buffer (50 mM HEPES, 100 mM KCl, 0.001% Tween-20, 5% DMSO, pH 7.4) was mixed with inhibitor at various concentrations and allowed to incubate for 30 minutes, after which trypsin and acetyl-Gly-Ala-(N-acetyl-Lys)-AMC were added to final concentrations of 50 nM and 25 μM, respectively, to initiate the reaction. Negative control reactions were performed in the absence of inhibitor in replicates of eight.

The reactions were monitored in a fluorescence plate reader. After a 30 minute lag time, the fluorescence was measured over a 30 minute time frame using an excitation wavelength of 355 nm and a detection wavelength of 460 nm. The increase in fluorescence with time was used as the measure of the reaction rate. Inhibition constants were obtained using the program BatchKi (Kuzmic et al. *Anal. Biochem.* 2000, 286, 45-50). Most of the compounds of this invention had a Ki of <10 nm.

Example 2

Cell proliferation Assay In Vitro

The ability of the compounds of Formula (I) to inhibit growth of tumor cells in vitro was determined as follows.

Stock cultures of the HCT116 colon carcinoma cell line were maintained in RPMI medium 1640 containing 10% (v/v) fetal bovine serum, 2 mM L-glutamine, 1 mM sodium pyruvate, 50 units/ml penicillin, and 50 μg/ml streptomycin at 37° C. in 5% CO$_2$ humidified atmosphere. Cells were cultured in 75-cm$^2$ culture flasks and subcultures were established every 3 to 4 days so as not to allow the cells to exceed 90% confluence.

HCT116 cells were harvested for proliferation assays by trypsinization (0.05% trypsin/0.53 mM EDTA), washed twice in culture medium, resuspended in appropriate volume of medium, and then counted using a hemacytometer. Cells were seeded in wells of flat-bottom 96-well plates at a density of 5,000 cell/well in 100 μl. Cells were allowed to attach for 1.5 to 2 hours at 37° C.

Compounds were diluted from 10 mM stock solutions in DMSO. Serial 3-fold dilutions were performed in medium containing 0.6% DMSO in wells (in triplicate) of a 96-well U-bottom plates starting with a 60 μM solution. After dilutions were completed, 100 μl of each compound dilution (in triplicate) was transferred to designated triplicate wells of the 96-well plate containing cells in 100 μl of medium. Final concentrations of the dose-response for compounds in assay plates ranged from 0.12 to 30 μM. Control wells (cells with no treatment) received 100 μl of 0.6% DMSO in culture medium. Wells containing medium with no cells served as the background wells. Cells were cultured with the compounds for 48 and 72 hours at 37° C. in a humidified $CO_2$ incubator.

Cell proliferation was assessed by measuring fluorescence after the addition of the fluorogenic redox indicator, Alamar Blue™ (BioSource International). Ten µl of Alamar Blue™ was added to each well of the 96-well plate(s) 3 to 4 hours prior to the end of the incubation period. Assay plates were read in a fluorescence plate reader (excitation, 530 nM; emission, 620 nM). $G_{150}$ values (concentration at which the growth of the tumor cells was inhibited by 50%) for compounds were determined by plotting the percent control fluorescence against the logarithm of the compound concentration. The compounds of this invention inhibited the growth of the tumor cells.

Pharmaceutical Composition Examples

The following are representative pharmaceutical formulations containing a compound of Formula (I)

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |

| Ingredient | Amount |
|---|---|
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 1.2 g |
| sodium acetate buffer solution, | 0.4 M 2.0 ml |
| HCl (1 N) or NaOH (1 N) | q.s. to suitable pH |
| water (distilled, sterile) | q.s. to 20 ml |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol™ H-15 (triglycerides of saturated vegetable fatty acid; Riches-Nelson, Inc., New York), and has the following composition:

| | |
|---|---|
| compound of the invention | 500 mg |
| Witepsol ™ H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

We claim:

1. A compound of Formula (I):

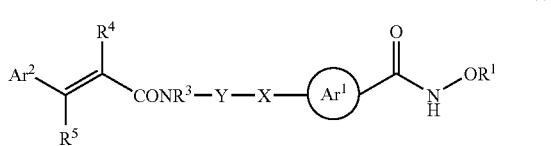

wherein:

$R^1$ is hydrogen or alkyl;

X is —O—

Y is alkylene;

$Ar^1$ is phenylene wherein said $Ar^1$ is optionally substituted with one or two groups independently selected from alkyl, halo, hydroxy, alkoxy, haloalkoxy, or haloalkyl;

$R^3$ is hydrogen, alkyl, hydroxyalkyl, or alkoxyalkyl;

$Ar^2$ is heteroaryl, wherein said $Ar^2$ is optionally substituted with one or two groups independently selected from alkyl, halo, haloalkyl, alkoxy, alkoxyalkyl, hydroxyalkoxy, hydroxyalkoxyalkyl, alkoxyalkyloxy, alkoxyalkyloxyalkyl, aminoalkyl, aminoalkoxy, haloalkoxy, haloalkoxyalkyl, optionally substituted phenylalkyl, optionally substituted phenyloxyalkyl, optionally substituted heteroaryl, optionally substituted heteroaralkyloxy, optionally substituted heteroaryloxyalkyl, optionally substituted heterocycloalkylalkyl, optionally substituted heterocycloalkyloxy, optionally substituted heterocycloalkylalkyloxy, -alkylene-$S(O)_nR^a$, where n is 0 to 2 and $R^a$ is hydroxyalkyl or optionally substituted phenyl, -alkylene-$NR^e$-alkylene $CONR^cR^d$, where $R^c$ is hydroxyl and $R^d$ and $R^e$ are independently hydrogen or alkyl, or carboxyalkylaminoalkyl; and one of $R^4$ and $R^5$ is hydrogen or alkyl and the other is —$CH_2R^6$ where $R^6$ is aryl, heteroaryl, heterocycloalkyl, hydroxyalkyloxy, alkoxyalkyloxy, aminoalkyloxy, aryloxy, aralkyloxy, heteroaryloxy, heteroaralkyloxy, heterocycloalkyloxy, heterocycloalkylalkyloxy, alkoxyalkyl-$S(O)_n$—, hydroxyalkyl-$S(O)_n$—, —$S(O)_n$-aryl, aralkyl-$S(O)_n$—, —$S(O)_n$-heteroaryl, heteroaralkyl-$S(O)_n$—, $S(O)_n$—, heterocycloalkyl, heterocycloalkylalkyl-$S(O)_n$—, where n is 0, 1, or 2, —$NR^7R^8$, where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl, —$NR^9SO_2R^{10}$, where $R^9$ is hydrogen or alkyl and $R^{10}$ is alkyl, aryl, aralkyl, heteroaryl, heteroaralkyl, heterocycloalkyl, or heterocycloalkylalkyl, or —$NR^{11}COR^{12}$, where $R^{11}$ is hydrogen or alkyl and $R^{12}$ is alkyl, aryl, aralkyl, heteroaryl, heteroaralkyl, heterocycloalkyl, or heterocycloalkylalkyl; or a pharmaceutically acceptable salt thereof.

2. The compound of claim 1 wherein $R^1$, $R^3$, and $R^4$ are hydrogen.

3. The compound of claim 1 wherein $R^1$, $R^3$, and $R^5$ are hydrogen.

4. The compound of claim 1 wherein $R^1$, $R^3$, and $R^4$ are hydrogen and $R^5$ is —$CH_2NR^7R^8$, where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl.

5. The compound of claim 1 wherein $R^1$, $R^3$, and $R^4$ are hydrogen and $R^5$ is —$CH_2$-heterocycloalkyl.

6. The compound of claim 1 wherein $R^1$, $R^3$, and $R^4$ are hydrogen, and $R^5$ is —$CH_2R^6$ where $R^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-$S(O)_n$—, hydroxyalkyl-$S(O)_n$—, —$S(O)_n$-aryl, aralkyl-$S(O)_n$—, —$S(O)_n$-heteroaryl, heteroaralkyl-$S(O)_n$—, —$S(O)_n$-heterocycloalkyl, heterocycloalkylalkyl-$S(O)_n$—, where n is 0, 1, or 2.

7. The compound of claim 1 wherein Y is ethylene, $R^1$, $R^3$, and $R^4$ are hydrogen, and $R^5$ is —$CH_2NR^7R^8$, where $R^7$ is hydrogen or alkyl and $R^8$ is alkyl, hydroxyalkyl, alkoxyalkyl, aryl, aralkyl, heteroaryl, heteroaralkyl, heterocycloalkyl, or heterocycloalkylalkyl.

8. The compound of claim 1 wherein Y is ethylene, $R^1$, $R^3$, and $R^4$ are hydrogen, and $R^5$ is —$CH_2$-heterocycloalkyl.

9. The compound of claim 1 wherein Y is ethylene, $R^1$, $R^3$, and $R^4$ are hydrogen, and $R^5$ is —$CH_2R^6$ where $R^6$ is hydroxyalkyloxy, alkoxyalkyloxy, aryloxy, aralkyloxy, heteroaryloxy, heteroaralkyloxy, heterocycloalkyloxy, heterocycloalkylalkyloxy, alkoxyalkyl-$S(O)_n$—, hydroxyalkyl-$S(O)_n$—, —$S(O)_n$-aryl, aralkyl-$S(O)_n$—, —$S(O)_n$-heteroaryl, heteroaralkyl-$S(O)_n$—, —$S(O)_n$-heterocycloalkyl, heterocycloalkylalkyl-$S(O)_n$—, where n is 0,1, or 2.

10. The compound of claim 7 wherein the heteroaryl of $Ar^2$ is benzofuran-2-yl optionally substituted with a substituent selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-ylmethoxy, 2-hydroxyethoxy, 2-N,N-dimethylaminoethoxy, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1,2,4-triazin-1-yl-phenoxymethyl, 2-phenylethyl, pyrrolidin-1-ylmethyl, piperidin-1-ylmethyl, 4-trifluoromethylpiperidin-ylmethyl, 4-methylpiperazin-ylmethyl, 3,3,3-trifluoropropyloxymethyl, 4-fluorophenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, N-methyl-N-2-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylamino-methyl); and the —CONHOH and X groups are at the 1 and 4 position of the phenylene ring.

11. The compound of claim 8 wherein the heteroaryl of $Ar^2$ is benzofuran-2-yl optionally substituted with a substituent selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-ylmethoxy, 2-hydroxyethoxy, 2-N,N-dimethylaminoethoxy, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1,2,4-triazin-1-yl-phenoxymethyl, 2-phenylethyl, pyrrolidin-1-ylmethyl, piperidin-1-ylmethyl, 4-trifluoromethylpiperidin-ylmethyl, 4-methylpiperazin-ylmethyl, 3,3,3-trifluoropropyloxy-methyl, 4-fluorophenylthiomethyl, 4-fluorophenylsulfinylmethyl, 4-fluorophenylsulfonyl-methyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, Ar-methyl-N-2-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylamino-methyl); and the —CONHOH and X groups are at the 1 and 4 position of the phenylene ring.

12. The compound of claim 9 wherein the heteroaryl of $Ar^2$ is benzofuran-2-yl optionally substituted with a substituent selected from chloro, fluoro, trifluoromethyl, methyl, ethyl, methoxy, 1-cyclopropylpiperidin-4-yloxy, 1-(2,2,2-trifluoroethyl)piperidin-4-yloxy, N,N-dimethylamino-methyl, N,N-diethylaminomethyl, 2-methoxyethoxymethyl, phenoxymethyl, 2-methoxyethoxy, 2-morpholin-4-ylethoxy, pyridin-3-ylmethoxy, 2-hydroxyethoxy, 2-N,N-dimethylaminoethoxy, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1,2,4-triazin-1-yl-phenoxy-methyl, 2-phenylethyl, pyrrolidin-1-ylmethyl, piperidin-1-ylmethyl, 4-trifluoromethyl-piperidin-ylmethyl, 4-methylpiperazin-ylmethyl, 3,3,3-trifluoropropyloxymethyl, 4-fluoro-phenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethyl-aminomethyl, 3-hydroxypropylthiomethyl, 3-hydroxypropylsulfinylmethyl, 3-hydroxypropyl-sulfonyl-methyl, N-methyl-N-2-indol-3-ylethylaminomethyl, 2-(4-trifluoromethylphenyl)ethyl, 2-(3-trifluoromethoxyphenyl)ethyl, AT-hydroxyaminocarbonyl-methylaminomethyl, or 3-(2-carboxyethylamino-methyl); and the —CONHOH and X groups are at the 1 and 4 position of the phenylene ring.

13. A pharmaceutical composition comprising a compound of claim 1 and a pharmaceutically acceptable excipient.

* * * * *